US008946172B2

(12) United States Patent
Mustoe et al.

(10) Patent No.: US 8,946,172 B2
(45) Date of Patent: Feb. 3, 2015

(54) METHOD FOR REDUCING SCARRING DURING WOUND HEALING USING ANTISENSE COMPOUNDS DIRECTED TO CTGF

(75) Inventors: Thomas A. Mustoe, Evanston, IL (US); Nicholas M. Dean, Encinitas, CA (US); Mark Sisco, New York, NY (US); Zol Kryger, Agoura Hills, CA (US); C. Frank Bennett, Carlsbad, CA (US)

(73) Assignees: Excaliard Pharmaceuticals, Inc., New York, NY (US); Isis Pharmaceuticals, Inc., Carlsbad, CA (US); Northwestern University, Evanston, IL (US)

( * ) Notice: Subject to any disclaimer, the term of this patent is extended or adjusted under 35 U.S.C. 154(b) by 428 days.

(21) Appl. No.: 12/547,481

(22) Filed: Aug. 26, 2009

(65) Prior Publication Data

US 2011/0054004 A1 Mar. 3, 2011

Related U.S. Application Data

(60) Provisional application No. 61/190,152, filed on Aug. 25, 2008.

(51) Int. Cl.
*A01N 43/04* (2006.01)
*C07H 21/04* (2006.01)

(52) U.S. Cl.
USPC .......... 514/44; 435/6.1; 435/91.1; 435/91.31; 435/455; 536/23.1; 536/24.5

(58) Field of Classification Search
USPC ................... 435/6, 91.1, 91.31, 455; 514/44; 536/23.1, 24.5
See application file for complete search history.

(56) References Cited

U.S. PATENT DOCUMENTS

| 4,508,040 | A | 4/1985 | Santen et al. |
| 5,408,040 | A | 4/1995 | Grotendorst et al. |
| 5,585,270 | A | 12/1996 | Grotendorst et al. |
| 5,783,187 | A | 7/1998 | Grotendorst et al. |
| 5,801,154 | A * | 9/1998 | Baracchini et al. ......... 514/44 A |
| 5,876,730 | A | 3/1999 | Brigstock et al. |
| 5,998,148 | A | 12/1999 | Bennett et al. |
| 6,069,006 | A | 5/2000 | Grotendorst et al. |
| 6,150,101 | A | 11/2000 | Grotendorst et al. |
| 6,232,064 | B1 | 5/2001 | Grotendorst et al. |
| 6,358,741 | B1 | 3/2002 | Schmidt et al. |
| 6,436,909 | B1 | 8/2002 | Dean et al. |
| 6,965,025 | B2 | 11/2005 | Gaarde et al. |
| 7,399,845 | B2 | 7/2008 | Seth et al. |
| 7,666,853 | B2 | 2/2010 | Khvorova et al. |
| 7,709,630 | B2 | 5/2010 | Gaarde et al. |
| 7,718,177 | B2 | 5/2010 | Grotendorst et al. |
| 7,820,809 | B2 | 10/2010 | Khvorova et al. |
| 7,833,989 | B2 | 11/2010 | Khvorova et al. |
| 2003/0050265 | A1 * | 3/2003 | Dean et al. ................ 514/44 |
| 2003/0119010 | A1 * | 6/2003 | Powell et al. ............. 435/6 |
| 2003/0153524 | A1 | 8/2003 | Hinton et al. |
| 2003/0180300 | A1 | 9/2003 | Grotendorst |
| 2003/0180891 | A1 | 9/2003 | Young et al. |
| 2005/0059629 | A1 * | 3/2005 | Gaarde et al. ............ 514/44 |
| 2005/0136502 | A1 | 6/2005 | Riser et al. |
| 2007/0299028 | A1 | 12/2007 | Siwkowski et al. |
| 2008/0015114 | A1 | 1/2008 | Khvorova et al. |
| 2008/0070856 | A1 | 3/2008 | Kreutzer et al. |
| 2008/0119433 | A1 | 5/2008 | Tabor |
| 2008/0125352 | A1 * | 5/2008 | Brigstock et al. ......... 514/2 |
| 2008/0193443 | A1 | 8/2008 | Beskrovnaya et al. |
| 2008/0206256 | A1 | 8/2008 | Spong et al. |
| 2009/0069623 | A1 | 3/2009 | Oh |
| 2009/0156524 | A1 | 6/2009 | Feinstein et al. |
| 2010/0130595 | A1 * | 5/2010 | Dean et al. .............. 514/44 R |
| 2010/0190838 | A1 * | 7/2010 | Grotendorst ............ 514/44 A |
| 2010/0266532 | A1 * | 10/2010 | Ferguson ................ 424/85.2 |
| 2011/0112168 | A1 | 5/2011 | Feinstein et al. |
| 2011/0237648 | A1 * | 9/2011 | Khvorova et al. ........ 514/44 A |

FOREIGN PATENT DOCUMENTS

| EP | 1461352 A2 | 9/2004 |
| EP | 2388318 A1 | 11/2011 |
| WO | WO 96/38172 A1 | 5/1996 |
| WO | WO 99/66959 A2 | 12/1999 |
| WO | WO 00/13706 A1 | 3/2000 |
| WO | 0027868 A2 | 5/2000 |
| WO | WO 00/27868 A2 | 5/2000 |
| WO | WO 00/35936 A1 | 6/2000 |
| WO | WO 00/35939 A2 | 6/2000 |
| WO | WO 01/29217 A2 | 4/2001 |
| WO | WO 01/85941 A2 | 11/2001 |
| WO | 0027868 A9 | 9/2002 |
| WO | 03053340 A2 | 7/2003 |
| WO | WO 2003/053340 A2 | 7/2003 |

(Continued)

OTHER PUBLICATIONS

Crooke, S. Ann Rev. Medicine, vol. 55, pp. 61-95 (2004).*
Perrachi et al., Rev. Med. Virol., vol. 14, pp. 47-64 (2004).*
Agrawal et al., Molecular Med. Today, vol. 6, pp. 72-81 (2000).*
Chirila et al., Biomaterials, vol. 23, pp. 321-342 (2002).*
Opalinska et al., Nature Re., vol. 1, pp. 503-514 (2002).*
Jang et al., Expert Rev. Medical Devices, vol. 1, No. 1, pp. 127-138 (2004).*
Igarashi et al, J. Invest. Dermatol., vol. 106, pp. 729-733 (1996).*
Colwell et al., Plast. Reconstr. Surg., vol. 116, pp. 1387-1390 (2005).*
Lu et al., J. Am. Coll. Surg., vol. 201, pp. 391-397 (2005).*
International Preliminary Report on Patentability issued Mar. 1, 2011 in connection with PCT International Application No. PCT/US2009/054975.

(Continued)

*Primary Examiner* — Jane Zara
(74) *Attorney, Agent, or Firm* — Lando & Anastasi LLP

(57) ABSTRACT

This invention provides a method for reducing hypertropic scarring resulting from dermal wound healing in a subject in need which comprises administering to the subject an antisense oligonucleotide which inhibits expression of connective tissue growth factor (CTGF) in an amount effective to inhibit expression of CTGF and thereby reduce hypertrophic scarring.

16 Claims, 13 Drawing Sheets

(56) References Cited

FOREIGN PATENT DOCUMENTS

| WO | 2004/099375 A2 | 11/2004 |
|---|---|---|
| WO | 2004099372 A2 | 11/2004 |
| WO | WO 2005/050202 A2 | 6/2005 |
| WO | WO 2005/050203 A2 | 6/2005 |
| WO | WO 2005/077413 A1 | 8/2005 |
| WO | WO 2005/110479 A2 | 11/2005 |
| WO | WO 2005/117941 A2 | 12/2005 |
| WO | WO 2005/120231 A1 | 12/2005 |
| WO | WO 2006/069037 A1 | 6/2006 |
| WO | WO 2006/122046 A2 | 11/2006 |
| WO | WO 2007/040636 A1 | 4/2007 |
| WO | 20081008772 A2 | 1/2008 |
| WO | WO 2008/050329 A2 | 5/2008 |
| WO | WO 2009/044392 A2 | 4/2009 |
| WO | WO 2010/027830 A2 | 3/2010 |
| WO | WO 2010/027831 | 3/2010 |
| WO | WO 2010/033246 A1 | 3/2010 |
| WO | WO 2010/036111 A1 | 4/2010 |
| WO | WO 2010/042201 A1 | 4/2010 |
| WO | WO 2010/042202 A1 | 4/2010 |
| WO | WO 2010/042281 A2 | 4/2010 |
| WO | WO 2010/107952 A2 | 9/2010 |
| WO | WO 2011/002525 A1 | 1/2011 |

OTHER PUBLICATIONS

Abreu JG, Ketpura NI, Reversade B, De Robertis EM. Connective-tissue growth factor (CTGF) modulates cell signaling by BMP and TGF-beta. *Nat Cell Biol* 2002;4(8):599-604.

Blalock TD, Duncan MR, Varela JC, Goldstein MH, Tuli SS, Grotendorst GR, et al. Connective tissue growth factor expression and action in human corneal fibroblast cultures and rat corneas after photorefractive keratectomy. *Invest Ophthalmol Vis Sci* 2003;44(5):1879-87.

Bonniaud P, Margetts PJ, Kolb M, Haberberger T, Kelly M, Robertson J, et al. Adenoviral gene transfer of connective tissue growth factor in the lung induces transient fibrosis. *Am J Respir Crit Care Med* 2003;168(7):770-8.

Colwell AS, Phan TT, Kong W, Longaker MT, Lorenz PH. Hypertrophic scar fibroblasts have increased connective tissue growth factor expression after transforming growth factor—beta stimulation. *Plast Reconstr Surg* 2005;116(5):1387-90; discussion 91-2.

Colwell AS, Krummel TM, Longaker MT, Lorenz HP. Fetal and adult fibroblasts have similar TGF-beta-mediated, Smad-dependent signaling pathways. *Plast Reconstr Surg* 2006;117(7):2277-83.

Dammeier J, Beer HD, Brauchle M, Werner S. Dexamethasone is a novel potent inducer of connective tissue growth factor expression. Implications for glucocorticoid therapy. *J Biol Chem* 1998;273(29):18185-90.

Frazier K, Williams S, Kothapalli D, Mapper H, Grotendorst GR. Stimulation of fibroblast cell growth, matrix production, and granulation tissue formation by connective tissue growth factor. *J Invest Dermatol* 1996;107(3):404-11.

Grotendorst GR. Connective tissue growth factor: a mediator of TGF-beta action on fibroblasts. *Cytokine Growth Factor Rev* 1997;8(3):171-9.

Grotendorst GR, Rahmanie H, Duncan MR. Combinatorial signaling pathways determine fibroblast proliferation and myofibroblast differentiation. *Faseb J* 2004;18(3):469-79'.

Igarashi A, Okochi H, Bradham DM, Grotendorst GR. Regulation of connective tissue growth factor gene expression in human skin fibroblasts and during wound repair. *Mol Biol Cell* 1993;4(6):637-45.

Igarashi A, Nashiro K, Kikuchi K, Sato S, Ihn H, Fujimoto M, et al. Connective tissue growth factor gene expression in tissue sections from localized scleroderma, keloid, and other fibrotic skin disorders. *J. Invest. Derma.* 1996;106(4):729-33.

Kryger ZB, Sisco M, Roy NK, Lu L, Rosenberg D, Mustoe TA. Temporal expression of the transfo ming growth factor—Beta pathway in the rabbit ear model of wound healing and scarring. *J Am Coll Surg* 2007;205(1):78-88.

Leask A, and Abraham DJ. TGF-beta signaling and the fibrotic response. *Faseb J* 2004;18(7):816-27.

Lin CG, Chen CC, Leu SJ, Grzeszkiewicz TM, Lau LF. Integrin-dependent functions of the angiogenic inducer NOV (CCN3): implication in wound healing. *J Biol Chem* 2005;280(9):8229-37.

Mustoe TA, Pierce GF, Morishima C, Deuel TF. Growth factor-induced acceleration of tissue repair through direct and inductive activities in a rabbit dermal ulcer model. *J Clin Invest* 1991;87(2):694-703.

Mustoe TA. Scars and keloids. *BMJ Clinical research ed* 2004;328(7452):1329-30.

Reid RR, Mogford JE, Butt R, deGiorgio-Miller A, Mustoe TA. Inhibition of procollagen C-proteinase reduces scar hypertrophy in a rabbit model of cutaneous scarring. *Wound Repair Regen* 2006;14(2):138-41.

Riser BL Denichilo M, Cortes P, Baker C, Grondin JM, Yee J, et al. Regulation of connective tissue growth factor activity in cultured rat mesangial cells and its expression in experimental diabetic glomerulosclerosis. *J Am Soc Nephrol* 2000;11(1):25-38.

Shi-wen X, Pennington D, Holmes A, Leask A, Bradham D, Beauchamp JR, et al. Autocrine overexpression of CTGF maintains fibrosis: RDA analysis of fibrosis genes in systemic sclerosis. *Exp Cell Res* 2000;259(1):213-24.

Shull MM, Ormsby I, Kier AB, Pawlowski S, Diebold RJ, Yin M, et al. Targeted disruption of the mouse transforming growth factor-beta 1 gene results in multifocal inflammatory disease. *Nature* 1992;359(6397):693-9.

Sisco M, Kryger ZB, Jia SC, Schultz GS, Dean NM, Mustoe TA. Antisense oligonucleotides against transforming growth factor-beta delay wound healing in a rabbit ear model. *J Am Coll Surg* 2005;201:S60.

Wang JF, Olson ME, Ma L, Brigstock DR, Hart DA. Connective tissue growth factor siRNA modulates mRNA levels for a subset of molecules in normal and TGF-beta 1-stimulated porcine skin fibroblasts. *Wound Repair Regen* 2004;12(2):205-16.

Zhang H, Cook J, Nickel J, Yu R, Stecker K, Myers K, et al. Reduction of liver Fas expression by an antisense oligonucleotide protects mice from fulminant hepatitis. *Nat Biotechnol* 2000;18(8):862-7; and.

International Search Report and Written Opinion issued Dec. 15, 2009 by the International Searching Authority in connection with International Application No. PCT/US2009/054975.

Adler et al., "Glomerular mRNAs in Human Type 1 Diabetes: Biochemical Evidence for Microalbuminuria as a Manifestation of Diabetic Nephropathy" Kidney International (2001) 2330-2336.

Allen, J.T. et al. (1999) "Enhanced insulin-like growth factor binding protein-related protein 2 (Connective tissue growth factor) expression in patients with idiopathic pulmonary fibrosis and pulmonary sarcoidosis," Am. J. Respir. Cell Mol. Biol. 21(6):693-70.

Allawi et al., "Mapping of RNA accessible sites by extension of random oligonucleotide libraries with reverse transcriptase" RNA (2001) 7:314-327.

Babic et al., "Fispl12/mouse connective tissue growth factor mediates endothelial cell adhesion and migration through integrin alphavbeta3, promotes endothelial cell survival and induces angiogenesis in vivo" Mol. Cell Biol. (1999) 19:2958-2966.

Boes et al., "Connective tissue growth factor (IGFBP-rP2) expression and regulation in cultured bovine endothelial cells" Endocrinology (1999) 140:1575-1580.

Bradham, D.M. et al. (1991) "Connective tissue growth factor: a cysteine-rich mitogen secreted by human vascular endothelial cells is related to the SRC-induced immediate early gene product CEF-10," J. Cell Biol., 114:1285-1294.

Duncan, M.R. et al. (1999) "Connective tissue growth factor mediates transforming growth factor β-induced collagen synthesis: down-regulation by cAMP," FASEB J. 1999 13:1774-1786.

Dunn et al., Accession No. AZ781130 on database rst.seq, Feb. 16, 2001.

Hishikawa, K. et al. (1999) "Connective Tissue Growth Factor Induces Apoptosis in Human Breast Cancer Cell Line MCF-7," J. Biol. Chem., 274:37461-37466.

Hishikawa, K. et al. (1999) "Transforming growth factor-β1 induces apoptosis via connective tissue growth factor in human aortic smooth muscle cells," Eur. J. Pharmacol., 385:287-290.

(56) References Cited

OTHER PUBLICATIONS

Hishikawa, K. at al. (2001) "Static Pressure Regulates Connective Tissue Growth Factor Expression in Human Mesangial Cells," J. Biol. Chem., 276:16797-16803.

Hillier et al., Accession No. R06912 on database rst.seq, Apr. 5, 1995.

Ho et al., "Mapping of RNA accessible sites for antisense experiments with oligonucleotide libraries" Nature Biotech. (1998) 16:59-63.

Ito, Y. et al. (2001) "Kinetics of Connective Tissue Growth Factor Expression during Experimental Proliferative Glomerulonephritis," J. Am. Soc . Nephrol., 12:472-484.

Kasaragod, A.B. et al. (2001) "Connective Tissue Growth Factor Expression in Pediatric Myofibroblastic Tumors," Pediatr. Dev. Pathol., 4:37-45.

Kondo, S. et al. (2000) "Characterization of a Mouse ctgf 3'-UTR Segment That Mediates Repressive Regulation of Gene Expression," Biochem. Biophys. Res. Commun., 278:119-124.

Kothapalli, D. et al. (1997) "Transforming growth factor beta induces anchorage-independent growth of NRK fibroblasts via a connective tissue growth factor-dependent signaling pathway," Cell Growth Diff., 8:61-68.

Jedsadayanmata et al., "Activation-dependent adhesion of human platelets to Cyr61 and Fisp12/mouse connective tissue growth factor is mediated through integrin alpha(IIb)beta(3)" J. Biol. Chem. (1999) 274:24321-24327.

Kim et al., "Identification of a family of low-affinity insulin-like growth factor binding proteins (IGEBPs) : characterization of connective tissue growth factor as a member of the IGFBP superfamily" PNAS (1997) 94:12981-12986.

Kubota, S. et al. (1999) "Involvement of cis-acting repressive element(s) in the 3'-untranslated region of human connective tissue growth factor gene," FEBS Lett., 450:84-88.

Lasky, J.A. et al. (1998) "Connective tissue growth factor mRNA expression is upregulated in bleomycin-induced lung fibrosis," Am. J. Physiol., 275:L365-L371.

Lau, L.F. et al. (1999) "The CCN Family of Angiogenic Regulators: The Integrin Connection," Exp. Cell Res., 248:44-57.

Lopez-Bermejo et al., "Characterization of insulin-like growth factor-binding protein-related proteins (IGFBP-rPs) 1, 2, and 3 in human prostate epithelial cells: potential roles for IGFBP-rP1 and 2 in senescence of the prostatic epithelium" Endocrinology (2000) 141:4072-4080.

Martinerie, C. et al. (1992) "Physical mapping of human loci homologous to the chicken nov proto-oncogene," Oncogene, 7:2529-2534 (Abstract only).

Moussad, E.A. et al. (2000) "Connective Tissue Growth Factor: What's in a Name?" Mol. Genet. Metab., 71:276-292.

Matveeva et al., "A rapid in vitro method for obtaining RNA accessibility patterns for complementary DNA probes: correlation with an intracellular pattern and known RNA structures" Nucleic Acids Res. (1997) 25:5010-5016.

Milner et al., "Selecting effective antisense reagents on combinatorial oligonucleotide arrays" Nature Biotech (1997) 15:537-541.

Nakanishi et al., "Overexpression of connective tissue growth factor/hypertrophic chondrocyte-specific gene products 24 decreases bone density in adult mice and induces dwarfism" Biochem. Biophys. Res. Commun. (2001) 281:678-681.

Patzel et al., "Theoretical design of antisense RNA structures substantially improves annealing kinetics and efficacy in human cells" Nature Biotech (1998) 16:64-68.

Patzel et al., "A theoretical approach to select effective antisense oligodeoxyribonucleotides at high statistical probability" Nucleic Acids Res. (1999) 27:4328-4334.

Pereira et al., "Transcriptional regulation of connective tissue growth factor by cortisol in osteoblasts" Am. J. Physiol. Endocrinol. Metab. (2000) 279:E570-E576.

Riser et al., "Urinary CCN (CTGF) as a Possible Predictor of Diabetic Nephropathy: Preliminary Report" Kidney International (2003) 64:451-458.

Santos et al, (2005) "Intraocular Delivery of Oligonucleotides," Curr. Pharm. Biotech., 6:7-15.

Shimo, T. et al. (1998) "Inhibition of Endogenous Expression of Connective Tissue Growth Factor by Its Antisense Oligonucleotide and Antisense RNA Suppresses Proliferation and Migration of Vascular Endothelial Cells," J. Biochem., 124:130-140.

Sisco et al. (2008) "Antisense Inhibition of Connective Tissue Growth Factor (CTGF/CCN2) mRNA Limits Hypertrophic Scarring Without Affecting Wound Healing In Vivo," Wound Rep. Reg. 16:661-673.

Tsubaki, J. et al. (2001) "Effects of sodium butyrate on expression of members of the IGF-binding protein superfamily in human mammary epithelial cells," J. Endocrinol., 169:97-110.

Twigg et al., "Advanced glycosylation end products up-regulate connective tissue growth factor (insulin-like growth protein-related protein 2) in human fibroblasts: a potential mechanism for expansion of extracellular matrix in diabetes mellitus" Endocrinology (2001) 142:1760-1769.

Vorwerk, P. et al. (2000) "CTGF (IGFBP-rP2) is specifically expressed in malignant lymphoblasts of patients with acute lymphoblastic leukaemia (ALL)," Brit. J. Cancer, 83:756-760.

Wahab et al., "Role of connective tissue growth factor in the pathogenesis of diabetic nephropathy" Biochem. J. (2001) 359:77-87.

Wahab et al., "Connective tissue growth factor and regulation of the mesangial cell cycle: role in cellular hypertrophy" J. Am. Soc. Nephrol. (2002) 13:2437-2445.

Walton et al., "Prediction of antisense oligonucleotide binding affinity to a structured RNA target" Biotechnology and Bioengineering (1999) 65:1-9.

Yang, D.H. et al. (1998) "Identification of Glycosylated 38- kDa Connective Tissue Growth Factor (IGFBP-Related Protein 2) and Proteolytic Fragments in Human Biological Fluids, and Up-Regulation of IGFBP-rP2 Expression by TGF-β in Hs578T Human Breast Cancer Cells," J. Clin. Endocrinol. Metab., 83:2593-2596.

Yokoi et al., "Role of connective tissue growth factor in profibrotic action of transforming growth factor-Beta: a potential target for preventing renal fibrosis" Am. J. Kidney Disease (2001) 38(4 Suppl. 1):S134-S138.

Yokoi et al., "Role of connective tissue growth factor in fibronectin expression and tubulointerstitial fibrosis" Am. J. Physiol. Renal Physiol. (2002) 282:F933-F942.

Office Action issued May 19, 2004 in connection with U.S. Appl. No. 10/006,191.

Response filed Sep. 20, 2004 in connection with U.S. Appl. No. 10/006,191.

Office Action issued Dec. 2, 2004 in connection with U.S. Appl. No. 10/006,191.

Response filed Feb. 2, 2005 in connection with U.S. Appl. No. 10/006,191.

Advisory Action issued Feb. 17, 2005 in connection with U.S. Appl. No. 10/006,191.

Office Action issued Apr. 17, 2007 in connection with U.S. Appl. No. 10/946,914.

Response filed Aug. 15, 2007 in connection with U.S. Appl. No. 10/946,914.

Office Action issued Oct. 31, 2007 in connection with U.S. Appl. No. 10/946,914.

Office Action issued May 26, 2009 in connection with U.S. Appl. No. 11/985,843.

Examiner Interview Summary issued Sep. 11, 2009 in connection with U.S. Appl. No. 11/985,843.

Response filed Nov. 27, 2009 in connection with U.S. Appl. No. 11/985,843.

Office Action issued Mar. 12, 2010 in connection with U.S. Appl. No. 11/985,843.

Preliminary Amendment filed Dec. 9, 2008 in connection with U.S. Appl. No. 12/011,761.

Office Action issued Jun. 17, 2011 in connection with U.S. Appl. No. 13/007,900.

Office Action issued Feb. 29, 2012 in connection with U.S. Appl. No. 13/329,095.

Office Action issued Jul. 7, 2011 in connection with U.S. Appl. No. 12/547,474.

(56) References Cited

OTHER PUBLICATIONS

Amendment in Response to Jul. 7, 2011 Office Action filed Oct. 4, 2011 in connection with U.S. Appl. No. 12/547,474.
Office Action issued Dec. 6, 2011 in connection with U.S. Appl. No. 12/547,474.
Amendment in Response to Dec. 6, 2011 Office Action filed Mar. 6, 2012 in connection with U.S. Appl. No. 12/547,474.
Notice of Allowance issued Mar. 12, 2012 in connection with U.S. Appl. No. 12/547,474.
Notice of Allowance issued Apr. 4, 2012 in connection with U.S. Appl. No. 12/547,474.
Communication issued Apr. 13, 2012 in connection with U.S. Appl. No. 12/547,474.
Daniels, et al., Mediation of transforming growth factor-beta1-stimulated matrix contraction by fibroblasts: A role for connective tissue growth factor in contractile scarring, American Journal of Pathology; [10640], Nov. 1, 2003 American Society for Investigative Pathology, US, vol. 163,Nr:5,pp. 2043-2052, (Nov. 2003).
European Search Report Dated Dec. 10, 2012 for Application No. 09812035.5.
Flanders K., et al "Interference with Transforming Growth Factor-beta/Smad3 Signaling Results in Accelerated Healing of Wounds in Previously Irradiated Skin" American Journal of Pathology. vol. 163, No. 6. Dec. 1, 2003.
Goa et al., "Connective tissue growth factor and pathological scar", Journal of Clinical Rehabilitative Tissue Engineering Research, Jun. 10, 2007. vol. 11,Nr:23,pp. 4606-4609.
Leask et al., "Targeting the TGFbeta, Endothelin-1 and CCN2 Axis to Combat Fibrosis in Scleroderma", Cellular Signalling, Elsevier Science Ltd, GB, vol. 20, No. 8, Aug. 1, 2008.
Leask et al., Insights Into the Molecular Mechanism of Chronic Fibrosis: The Role of Connective Tissue Growth Factor in Scleroderma, Journal of Investigative Dermatology, Jan. 1, 2004 Nature Publishing Group, GB , vol. 122,Nr:1,pp. 1-06.
Leask, Transcriptional profiling of the scleroderma fibroblast reveals a potential role for connective tissue growth factor (CTGF) in pathological fibrosis,The Keio Journal of Medicine, Jan. 1, 2004 School of Medicine, Keio University , vol. 53, Nr:2,pp. 74-77.
Osamu, et al., "Connective tissue growth factor modulates extracellular matrix production in human subconjunctival fibroblasts and their proliferation and migration in vitro", Japanese Journal of Ophthalmology, Mar. 28, 2008, vol. 52, Nr:1,pp. 8-15.
Ren, et al., Effects of antisense oligonucleotides on expression of connective tissue growth factor and collagen synthesis in human hyperplastic scar fibroblast, Chinese Journal of Clinical Rehabilitation, vol. 10,Nr:16,pp. 92-94, (2008).
Shi-Wen, et al., Regulation and function of connective tissue growth factor/CCN2 in tissue repair, scarring and fibrosis, Cytokine and Growth Factor Reviews, Mar. 19, 2008 Elsevier Ltd, GB , vol. 19,Nr:2,pp. 133-144.
Sisco et al. (2008) "Antisense Inhibition of Connective Tissue Growth Factor (CTGF/CCN2} mRNA Limits Hypertrophic Scarring Without Affecting Wound Healing In Vivo," Wound Rep. Reg. 16:661-673.
Supplementary European Search Report dated Dec. 3, 2012 for EP 09812035.
Xu M. et al., "Effects of Antisense Oligonucleotide of Connective Tissue Growth Factor on Apoptosis of Hypertrophic Scar Fibroblasts and the Related Mechanism" Academic Journal of Second Military Medical University, vol. 28, No. 8. Aug. 1, 2007.

* cited by examiner

Figure 2
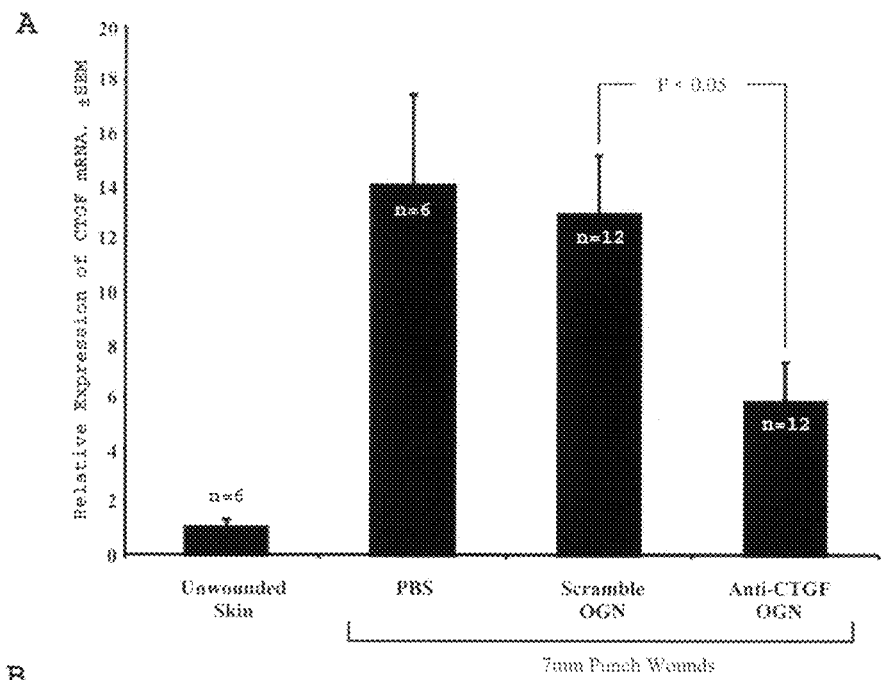
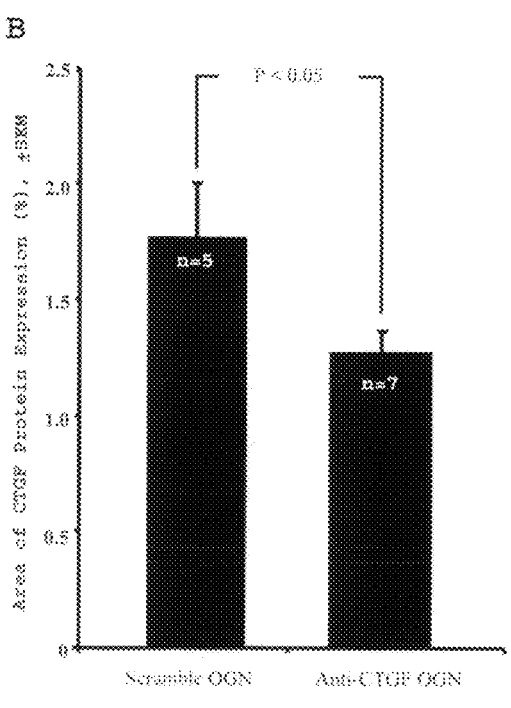
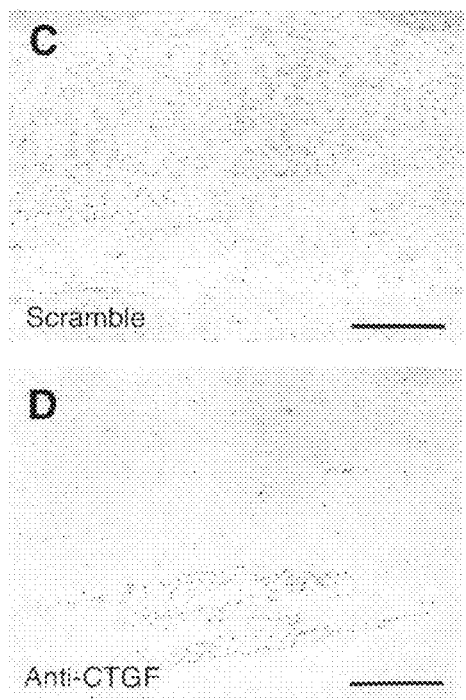

Figure 3
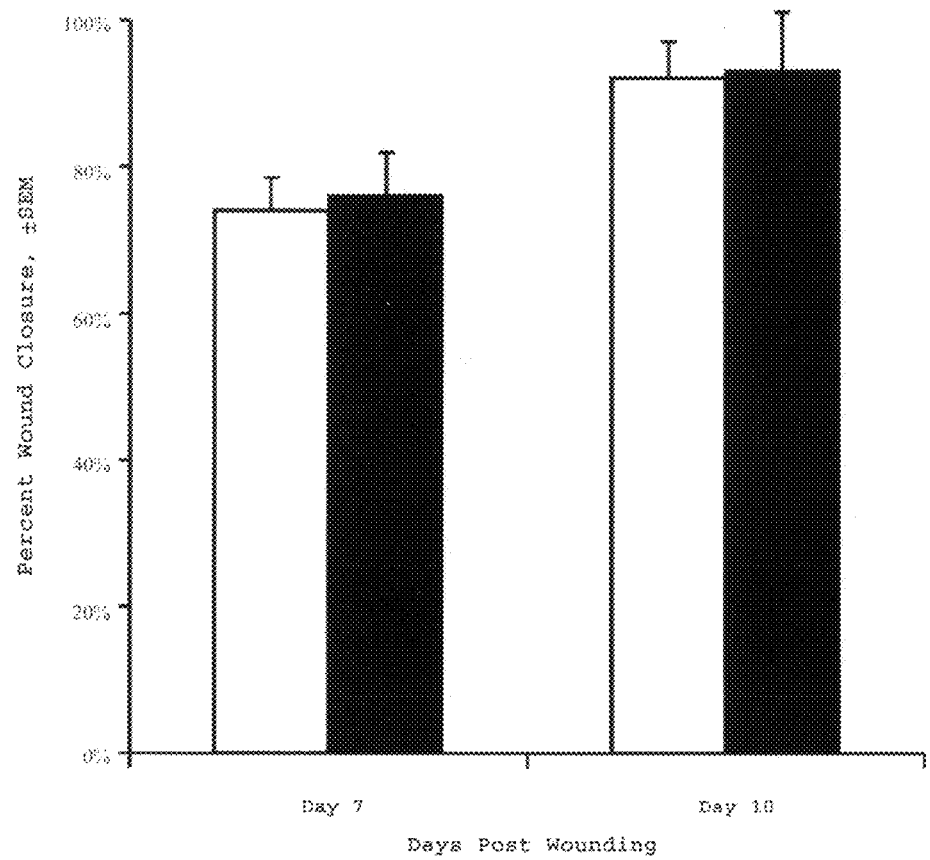
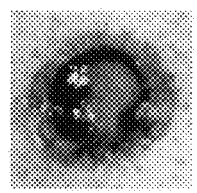 Scramble OGN (n=18)
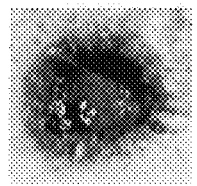 Anti-CTGF OGN (n=18)

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Antisense oligonucleotide directed to human
      CTGF

<400> SEQUENCE: 1
ccacaagctg tccagtctaa                                                 20

<210> SEQ ID NO 2
<211> LENGTH: 20
<212> TYPE: DNA
<213> ORGANISM: Artificial Sequence
<220> FEATURE:
<223> OTHER INFORMATION: Antisense oligonucleotide directed to human
      CTGF

<400> SEQUENCE: 2
aaacatgtaa cttttggtca                                                 20

<210> SEQ ID NO 3
<211> LENGTH: 20
<212> TYPE: DNA
<213> ORGANISM: Artificial Sequence
<220> FEATURE:
<223> OTHER INFORMATION: Antisense oligonucleotide directed to TGF-Beta
      1

<400> SEQUENCE: 3
gtccaccatt agcacgcggg                                                 20
```

METHOD FOR REDUCING SCARRING DURING WOUND HEALING USING ANTISENSE COMPOUNDS DIRECTED TO CTGF

This application claims benefit of U.S. Provisional Application No. 61/190,152, filed Aug. 25, 2008, the contents of which are hereby incorporated by reference.

This invention was made with government support under grant number R01 GM063825 awarded by the National Institutes of Health. The government has certain rights in the invention.

Throughout this application, certain patents, patent applications, and publications are referenced by patent number, application number, and for the latter, by authors and publication date. Full citations for these publications may be found at the end of this specification immediately preceding the claims. The disclosures of these documents in their entireties are hereby incorporated by reference into this application in order to more fully describe the state of the art to which this invention relates.

FIELD OF INVENTION

The present invention relates to reducing scarring resulting from wound healing.

BACKGROUND OF THE INVENTION

Dermal Wound Healing Process

Dermal wound healing is a complex process that, when properly orchestrated, leads to reestablishment of skin integrity with minimal residual scarring. Normal wound healing includes a transition from a proliferative phase, during which extracellular matrix (ECM) proteins are elaborated, to a remodeling phase, during which the wound is strengthened through stromal organization. Abnormal wound healing may result in pathologic dermal scarring, which represents a diverse spectrum of disorders that range from unsightly scars, to keloids, to life-threatening systemic diseases such as scleroderma. One example of pathologic dermal scarring is hypertrophic scars that are an unfavorable outcome of burns, trauma, or surgery. Although much has been learned about the pathophysiology of pathologic dermal scarring, most treatment modalities lack a defined mechanism of action, are non-specific, and have limited efficacy (Mustoe 2004). Indeed to date, there are no FDA approved drugs to treat dermal scarring.

The Roles of Transforming Growth Factor-Beta (TGF-β) and Connective Tissue Growth Factor (CTGF)

There is widespread evidence that dysregulation of the transforming growth factor-beta (TGF-β) family leads to scarring in a variety of chronic inflammatory conditions and in response to acute injury. (Shah et al. 1995; Leask and Abraham 2004) As such, TGF-β has been the target of many therapeutic approaches designed to limit acute and chronic fibrosis. However, since TGF-β plays pleiotrophic physiologic roles, efforts to modulate it have been limited by concerns about treatment specificity. (Shull et al. 1992) For example, neutralization of TGF-β reduces fibrosis in animal models of surgical scarring (Lu et al. 2005; Shah et al. 1992) but has also delayed wound healing. (Sisco et al. 2005)

Another growth factor of interest is connective tissue growth factor (CTGF), which is a matricellular protein that is known to regulate aspects of cell proliferation, migration, differentiation, angiogenesis, ECM production, and adhesion. (Frazier et al. 1996) Overexpression of CTGF mRNA and protein has been observed in chronic fibrotic disorders affecting multiple organ systems. In the skin, the role of CTGF in fibrosis is becoming better defined. Although CTGF has minimal basal expression in normal skin, it demonstrates transient up-regulation for several days following dermal injury. (Lin et al, 2005; Igarashi et al. 1993; Dammeier et al. 1998) In contrast, persistent overexpression of CTGF has been observed in biopsies of keloids and localized sclerosis. (Igarashi et al. 1996) Fibroblasts cultured from hypertrophic scars, keloids, and scleroderma lesions express increased basal CTGF. (Colwell et al. 2006; Shi-Wen et al. 2000) In addition, cells cultured from hypertrophic scars elaborate more CTGF in response to stimulation with TGF-β. (Colwell et al. 2005)

Since TGF-β potently induces CTGF through several pathways, CTGF has long been thought to mediate many of its fibrotic effects. Indeed, studies in various cell populations have demonstrated roles for CTGF in the TGF-β-dependent induction of fibronectin (Fn), collagen, and tissue inhibitor of metalloproteinase-1 (TIMP-1). (Frazier et al. 1996; Blalock et al. 2003; Grotendorst 1997; Wang et al. 2004) A more recent paradigm suggests that CTGF functions as a co-factor to TGF-β by enhancing ligand-receptor binding in activated cells. (Abreu et al. 2002) This may explain research that shows a limited ability of CTGF to induce ECM production and sustained fibrosis in vivo in the absence of TGF-β. (Frazier et al. 1996; Bonniaud et al. 2003; Mori et al. 1999) In addition, while CTGF mediates the effects of TGF-β on myofibroblast differentiation, it is insufficient to bring about this change when introduced exogenously (Folger et al. 2001).

There are several examples whereby TGF-β-independent induction of CTGF may contribute to its pathologic activity. Mechanical stress induces CTGF expression directly (Garrett 2004; Kessler et al. 2001; Schild et al. 2002). Elevated expression of CTGF, without a concomitant rise in TGF-β, has been observed in response to several factors known to contribute to healing, such as thrombin, factor VIIa, and exogenous CTGF. Furthermore, endothelin-1, epidermal growth factor, fibroblast growth factor, vascular endothelial growth factor, and platelet-derived growth factor can independently initiate transcription of CTGF in fibroblasts.

CTGF may be an attractive target for modulating hypertrophic scarring for several reasons. As a cofactor and downstream mediator of TGF-β, CTGF may represent a more specific target than TGF-β for gene-directed molecular therapies aimed at scarring, particularly since TGF-β has pluripotent effects unrelated to scar formation. In addition, CTGF may have TGF-β independent functions in maintaining a fibrotic phenotype that would be neglected by anti-TGF-β strategies. Despite advances in understanding CTGF's roles in augmenting fibrosis in multiple organ systems and in chronic dermal diseases such as scleroderma, CTGF's roles in acute scarring and wound healing remain largely observational.

To determine whether CTGF was necessary for wound healing and scar hypertrophy, a study was conducted whereby CTGF was specifically blocked in well-characterized rabbit models. The goal of the study was also to determine mechanisms whereby CTGF might be exerting its effect. The hypothesis was that inhibition of CTGF expression in vivo would abrogate fibrosis without having a detrimental effect on wound closure, a finding that has not been previously shown in skin by others.

The Role of Antisense Oligonucleotide

Antisense technology is an effective means for reducing the expression of specific gene products and may be uniquely useful in a number of therapeutic, diagnosic, and research applications for the modulation of connective tissue factor expression. (Garde et al., 2005, U.S. Pat. No. 6,965,025B2)

An antisense compound is an oligomeric compound that is capable of undergoing hybridization to a target nucleic acid (e.g. target mRNA).

Antisense compounds, compositions and methods for modulating expression of connective tissue growth factor and for treatment of disease associated with expression of connective tissue growth factor are disclosed intra alia in U.S. Pat. No. 6,965,025B2.

SUMMARY OF THE INVENTION

The present invention provides a method for reducing hypertropic scarring resulting from dermal wound healing in a subject in need thereof which comprises administering to the subject an antisense compound particularly an antisense oligonucleotide which inhibits expression of connective tissue growth factor (CTGF) in an amount effective to inhibit expression of CTGF and thereby reduce hypertrophic scarring.

BRIEF DESCRIPTION OF THE FIGURES

FIG. 2 shows that antisense oligonucleotides directed against CTGF reduce CTGF mRNA expression and protein staining in vivo. 300 µg of anti-CTGF oligonucleotide or scramble oligonucleotide was injected at days 14, 19, and 24. Scars were harvested at day 28. FIG. 2A shows the levels of CTGF mRNA expression measured by real-time polymerase chain reaction (RT-PCR). PBS in the figure stands for phosphate-buffered saline. FIG. 2B shows that CTGF protein staining, in which anti-CTGF antibody-stained sections were digitally analyzed for color density, which is expressed as percent staining relative to scar area. FIG. 2C shows a photograph of a scramble-oligonucleotide-treated scar. FIG. 2D shows a photograph of an anti-CTGF-treated scar with the scale bar of 0.25 mm.

FIG. 3 shows that gross wound closure, as determined photometrically, was similar in antisense- and scramble-treated wounds at post-wounding days 7 and 10. The photographs depict representative wounds at day 7 at a resolution of 66×100 mm or 600×600 DPI.

FIG. 4A shows the area of granulation tissue deposition FIG. 4B shows epithelialization as assessed by measuring the gap between the inward-migrating epithelium. FIG. 4C shows representative scramble control ASO-treated wound at day 10 in a photograph of the histology sample. FIG. 4D representative anti-CTGF-ASO treated wound at day 10 in a photograph of the histology sample. The scale bar is 1 mm. Hematoxylin and eosin stain was used in the sample preparation. These results clearly demonstrate that treatment with an ASO inhibitor of CTGF expression has no effect on the early wound healing response subsequent to the generation of a wound, even though this treatment reduces subsequent severity of hypertrophic scarring.

FIG. 5A shows that early and late blockade of CTGF reduced scar hypertrophy. The scar elevation index was assessed at day 28 post-wounding. FIG. 5B concerns the effort of administering antisense oligonucleotides at days 0, 5, and 10 (early treatment cohort) versus administration at days 14, 19, and 24 (late treatment cohort, (FIG. 5D). FIG. 5B shows the result for control scramble oligonucleotides. The scale bar is 1 mm. Hematoxylin and eosin stain was used in the sample preparation. FIGS. 5B to 5D are photographs of the stained specimens. FIG. 5E provides the formula for calculating a scar elevation index (SEI) as a measurement of the severity of the scarring.

DETAILED DESCRIPTION OF THE INVENTION

Figure 1:
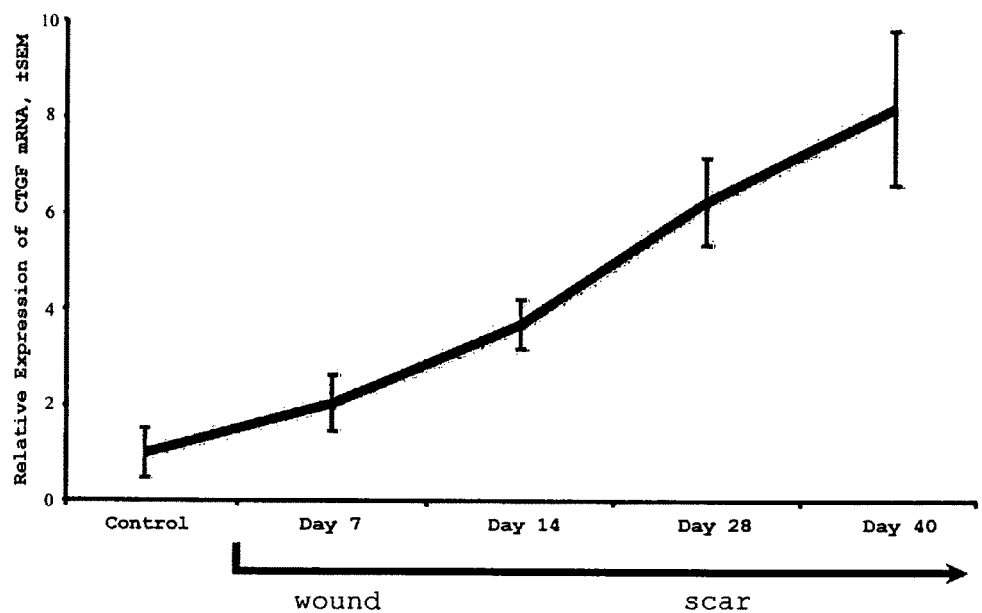
FIG. 1 shows that CTGF mRNA expression in a rabbit ear hypertrophic scar model continues to increase through day 40 in scar-forming wounds. mRNA levels are expressed relative to levels found in unwounded skin. The sample size is 6 wounds per time point (N=6).

This invention provides a method for reducing hypertropic scarring resulting from dermal wound healing in a subject in need thereof which comprises administering to the subject an antisense compound, such as a modified antisense oligonucleotide, particularly an oligodeoxyribonucleotide, or an siRNA compound which inhibits expression of connective tissue growth factor (CTGF) in an amount of such oligonucleotide effective to inhibit expression of CTGF in the subject.

In the practice of the method of this invention the subject may be an animal, preferably a human.

In one embodiment the method of the invention involves administering antisense oligonucleotide consisting of 12 to 30 nucleosides targeted to a nucleic acid encoding connective tissue growth factor (See SEQ ID NO:19 in U.S. Pat. No. 6,965,025 B2), wherein the oligonucleotide specifically hybridizes with said nucleic acid and inhibits expression of connective tissue growth factor, wherein said oligonucleotide comprises at least one modification selected from the group consisting of a modified internucleoside linkage, a modified sugar, and a modified nucleobase. Examples of suitable antisense oligonucleotides are described in aforementioned U.S. Pat. No. 6,965,025, two of which are presently preferred, i.e. the oligonucleotides having the sequence set forth in SEQ ID No.:39 or 48, i.e. SEQ ID NOs: 1 or 2 herein, respectively.

Although antisense oligonucleotides containing a variety of modified internucleoside linkages may be employed, the currently preferred modified internucleoside linkage is a phosphothioate linkage between one or more of the nucleosides. Modified oligonucleotides may also contain one or more nucleosides having modified sugar moieties. For example, the furanosyl sugar ring can be modified in a number of ways including substitution with a substituent group, bridging to form a BNA and substitution of the 4'-O with a heteroatom such as S or N(R) as described in U.S. Pat. No. 7,399,845 to Seth et al., hereby incorporated by reference herein in its entirety.

In general, it is preferred that the antisense oligonucleotide contains at least one and typically more than one modified sugar. Although various modified sugars may be employed it is presently preferred to employ a 2'-O-methoxyethyl sugar.

Modified oligonucleotides may also contain one or more substituted sugar moieties. For example, the furanosyl sugar ring can be modified in a number of ways including substitution with a substituent group, bridging to form a bicyclic nucleic acid "BNA" and substitution of the 4'-O with a heteroatom such as S or N(R) as described in U.S. Pat. No. 7,399,845 to Seth et al., hereby incorporated by reference herein in its entirety. Other examples of BNAs are described in published International Patent Application No. WO 2007/146511, hereby incorporated by reference herein in its entirety.

Antisense compounds of the invention can optionally contain one or more nucleotides having modified sugar moieties. Sugar modifications may impart nuclease stability, binding affinity or some other beneficial biological property to the antisense compounds. The furanosyl sugar ring of a nucleoside can be modified in a number of ways including, but not limited to: addition of a substituent group, particularly at the 2' position; bridging of two non-geminal ring atoms to form a bicyclic nucleic acid (BNA); and substitution of an atom or group such as —S—, —N(R)— or —C(R1)(R2) for the ring oxygen at the 4'-position. Modified sugars include, but are not limited to: substituted sugars, especially 2'-substituted sugars having a 2'-F, 2'-OCH2 (2'-OMe) or a 2'-O(CH2)2-OCH3 (2'-O-methoxyethyl or 2'-MOE) substituent group; and bicyclic modified sugars (BNAs), having a 4'-(CH2)n-O-2' bridge, where n=1 or n=2. Methods for the preparations of modified sugars are well known to those skilled in the art.

In certain embodiments, a 2'-modified nucleoside has a bicyclic sugar moiety. In certain such embodiments, the bicyclic sugar moiety is a D sugar in the alpha configuration. In certain such embodiments, the bicyclic sugar moiety is a D sugar in the beta configuration. In certain such embodiments, the bicyclic sugar moiety is an L sugar in the alpha configuration. In certain such embodiments, the bicyclic sugar moiety is an L sugar in the beta configuration.

In certain embodiments, the bicyclic sugar moiety comprises a bridge group between the 2' and the 4'-carbon atoms. In certain such embodiments, the bridge group comprises from 1 to 8 linked biradical groups. In certain embodiments, the bicyclic sugar moiety comprises from 1 to 4 linked biradical groups. In certain embodiments, the bicyclic sugar moiety comprises 2 or 3 linked biradical groups. In certain embodiments, the bicyclic sugar moiety comprises 2 linked biradical groups. In certain embodiments, a linked biradical group is selected from —O—, —S—, —N(R1)-, —C(R1)(R2)-, —C(R1)=C(R1)-, —C(R1)=N—, —C(=NR1)-, —Si(R1)(R2)-, —S(=O)2-, —S(=O)—, —C(=O)— and —C(=S)—; where each R1 and R2 is, independently, H, hydroxyl, C1-C12 alkyl, substituted C1-C12 alkyl, C2-C12 alkenyl, substituted C2-C12 alkenyl, C2-C12 alkynyl, substituted C2-C12 alkynyl, C5-C20 aryl, substituted C5-C20 aryl, a heterocycle radical, a substituted hetero-cycle radical, heteroaryl, substituted heteroaryl, C5-C7 alicyclic radical, substituted C5-C7 alicyclic radical, halogen, substituted oxy (—O—), amino, substituted amino, azido, carboxyl, substituted carboxyl, acyl, substituted acyl, CN, thiol, substituted thiol, sulfonyl (S(=O)2-H), substituted sulfonyl, sulfoxyl (S(=O)—H) or substituted sulfoxyl; and each substituent group is, independently, halogen, C1-C12 alkyl, substituted C1-C12 alkyl, C2-C12 alkenyl, substituted C2-C12 alkenyl, C2-C12 alkynyl, substituted C2-C12 alkynyl, amino, substituted amino, acyl, substituted acyl, C1-C12 aminoalkyl, C1-C12 aminoalkoxy, substituted C1-C12 aminoalkyl, substituted C1-C12 aminoalkoxy or a protecting group.

In some embodiments, the bicyclic sugar moiety is bridged between the 2' and 4' carbon atoms with a biradical group selected from —O—(CH$_2$)p-, —O—CH$_2$—, —O—CH$_2$CH$_2$—, —O—CH(alkyl)-, —NH—(CH$_2$)p-, —N(alkyl)-(CH$_2$)p-, —O—CH(alkyl)-, —(CH(alkyl))-(CH$_2$)p-, —NH—O—(CH$_2$)p-, —N(alkyl)-O—(CH$_2$)p-, or —O—N(alkyl)-(CH$_2$)p-, wherein p is 1, 2, 3, 4 or 5 and each alkyl group can be further substituted. In certain embodiments, p is 1, 2 or 3.

In one aspect, each of said bridges is, independently, —[C(R1)(R2)]n-, —[C(R1)(R2)]n-O—, —C(R1R2)-N(R1)-O— or —C(R1R2)-O—N(R1)-. In another aspect, each of said bridges is, independently, 4'-(CH$_2$)3-2', 4'-(CH$_2$)2-2', 4'-CH$_2$—O-2', 4'-(CH$_2$)2-O-2', 4'-CH$_2$—O—N(R1)-2' and 4'-CH$_2$—N(R1)-O-2'- wherein each R1 is, independently, H, a protecting group or C1-C12 alkyl.

In nucleotides having modified sugar moieties, the nucleobase moieties (natural, modified or a combination thereof) are maintained for hybridization with an appropriate nucleic acid target.

In one embodiment, antisense compounds targeted to a nucleic acid comprise one or more nucleotides having modified sugar moieties. In a preferred embodiment, the modified sugar moiety is 2'-MOE. In other embodiments, the 2'-MOE modified nucleotides are arranged in a gapmer motif.

Currently preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C$_1$ to C$_{10}$ alkyl or C$_2$ to C$_{10}$ alkenyl and alkynyl. Particularly preferred are O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10. Other preferred oligonucleotides comprise one of the following at the 2' position: C$_1$ to C$_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties.

Currently preferred modifications include 2'-methoxyethoxy (2'-O—CH$_2$CH$_2$OCH$_3$, also known as 2'-O-(2-methoxyethyl) or 2'-MOE) (Martin et al., Helv. Chim. Acta, 1995, 78, 486-504) i.e., an alkoxyalkoxy group. A further preferred modification includes 2'-dimethylaminooxyethoxy, i.e., a O(CH$_2$)$_2$ON(CH$_3$)$_2$ group, also known as 2'-DMAOE, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$)$_2$.

A further currently preferred modification of the sugar includes bicyclic nucleic acid (also referred to as locked nucleic acids (LNAs)) in which the 2'-hydroxyl group is linked to the 3' or 4' carbon atom of the sugar ring, thereby forming a bicyclic sugar moiety. The linkage is preferably a methylene (—CH$_2$—)$_n$ group bridging the 2' oxygen atom and the 4' carbon atom wherein n is 1 or 2 including α-L-Methyleneoxy (4'-CH2-O-2') BNA, β-D-Methyleneoxy (4'-CH2-O-2') BNA and Ethyleneoxy (4'-(CH2)$_2$-O-2') BNA. Bicyclic modified sugars also include (6'S)-6'methyl BNA, Aminooxy (4'-CH2-O—N(R)-2') BNA, Oxyamino (4'-CH2-N(R)—O-2') BNA wherein, R is, independently, H, a protecting group, or C1-C12 alkyl. LNAs also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands.

LNAs in which the 2'-hydroxyl group is linked to the 4' carbon atom of the sugar ring thereby forming a 2'-C,4'-C-oxymethylene linkage thereby forming a bicyclic sugar moiety. The linkage may be a methylene (—CH$_2$—)$_n$ group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10° C.), stability towards 3'-exonucleolytic degradation and good solubility properties. Other preferred bridge groups include the 2'-deoxy-2'-CH$_2$OCH$_2$-4' bridge. LNAs and preparation thereof are described in published International Patent Application Nos. WO 98/39352 and WO 99/14226.

Other currently preferred modifications include 2'-methoxy (2'-O—CH$_3$), 2'-aminopropoxy (2'-OCH$_2$CH$_2$CH$_2$NH$_2$), 2'-allyl (2'-CH$_2$—CH═CH$_2$); 2'-O-allyl (2'-O—CH$_2$—CH═CH$_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; and 6,600,032 each of which is hereby incorporated by reference herein in its entirety. A representative list of preferred modified sugars includes but is not limited to substituted sugars having a 2'-F, 2'-OCH$_2$ or a 2'-O(CH$_2$)$_2$—OCH$_3$ substituent group; 4'-thio modified sugars and bicyclic modified sugars.

In a further embodiment, the method of the invention provides that at least one and typically more than one of the nucleobases contained in the antisense oligonucleotide will be a modified nucleotide such as a 5-methylcytosine.

In one embodiment of the method of this invention the antisense oligonucleotide is administered commencing no sooner than 7 days after the subject is wounded, preferably commencing about 14 days after the subject is wounded and continuing thereafter during the period of wound healing. Wounding can be induced by (but not limited to) the following: skin injury, skin abrasions, elective surgery, reconstructive surgery, general surgery, burns, cosmetic surgery and any injury which results in breakage or damage to the skin. Alternatively, the oligonucleotides may be administered commencing immediately before or after the subject is wounded. In certain embodiments of the invention the method further comprises administering to the subject an antisense oligonucleotide which inhibits expression of transforming growth factor β1 (TGF β1) in addition to the antisense oligonucleotide which inhibits expression of CTGF. Examples of suitable antisense oligonucleotides to TGF β1 are described in U.S. Pat. No. 6,436,909, one of which are presently preferred, i.e. the oligonucleotide having the sequence set forth in SEQ ID No:13, herein incorporated by reference as SEQ ID No:3.

In the method of this invention a second antisense oligonucleotide which inhibits expression of connective tissue growth factor may also be administered. In certain embodiments, the co-administration of the second antisense oligonucleotide enhances the effect of the first antisense oligonucleotide, such that co-administration results in an effect that is greater than the effect of administering each alone.

Various regimes may be employed in the practice of the method of this invention for administering antisense oligonucleotides including simultaneous and sequential dosing regimens. For example, the ASO which inhibits expression of connective tissue growth factor may be administered intermittently with each subsequent administrations being effected at least 4 days after the prior administration.

In the methods of this invention the antisense oligonucleotide is desirably administered in an amount effective to reduce scarring without having an adverse effect on wound healing, e.g. an amount between about 300 μg/cm and about 10 mg/cm of the wound, preferably between 250 μg/cm and 5 mg/cm; being preferably between 500 μg/cm and 5 mg/cm.

In one embodiment of the invention, wherein the amount of antisense oligonucleotide administered is between 100 μg/cm and 10 mg/cm of the wound.

In another embodiment of the invention, where in the amount of antisense oligonucleotide administered is above 300 μg/cm.

In a further embodiment of the invention, wherein the antisense oligonucleotide is administered in an amount effective to reduce scarring without having an effect on wound healing.

This invention also provides a method for reducing hypertropic scarring resulting from dermal wound healing in a subject in need thereof which comprises administering to the subject an antisense compound which inhibits expression of transforming growth factor-beta 1 (TGF-β1) in an amount effective to inhibit expression of TGF-β1 and thereby reduce hypertrophic scarring.

This invention is illustrated in the Experimental Details section which follows. This section is set forth to aid in an understanding of the invention but is not intended to, and should not be construed to, limit in any way the invention as set forth in the claims set forth hereinafter.

EXAMPLES

Example 1

Antisense Inhibition of Connective Tissue Growth Factors (CTGF/CCN2) mRNA Limits Hypertrophic Scarring Without Affecting Wound Healing In Vivo Introduction This study assesses the importance of CTGF to wound repair and hypertrophic scarring and evaluate its suitability as a target for anti-scarring therapies. The data demonstrate that modified antisense oligonucleotides against CTGF reduce hypertrophic scarring in an animal (rabbit) model.

Materials and Methods

Preparing Antisense Oligonucleotides to CTGF

Human, mouse, and rat CTGF cDNA were analyzed for unique 20-mer nucleotide sequences with highGC contents to minimize self-hybridization and provide stability of the oligonucleotide mRNA complex. Twenty-mer phosphorothioate oligonucleotides containing 2'-O-methoxyethyl (2'MOE) modifications at positions 1-5 and 15-20, and oligonucleotides at positions 6-14 were used for all experiments. For each gene target, a series of 36 different antisense oligonucleotides, including deoxyribonucleotides, was designed to hybridize to sequences throughout the mRNA. Oligonucleotides were synthesized as previously described (McKay et al. 1999) and were screened as described below.

Primary cultures of early (3 to 4) passage rabbit dermal fibroblasts were grown to confluence and then treated with 150 nmol/L of oligonucleotide and 10 µg/ml of lipofectin (Life Technologies, Inc, Rockville, Md.) for 4 hours. The cells were washed and grown for 24 hours, after which total RNA was isolated from the cells using the RNeasy mini kit (Qiagen, Inc., Valencia, Calif.) per the manufacturer's protocol. CTGF mRNA expression was measured using real-time RT PCR as described below. The relative CTGF mRNA levels from the RT-PCR analysis were determined after normalization to 18S RNA levels. The oligodeoxynucleotide at target site 1707 in the 3'UTR of CTGF reduced the level of CTGF mRNA in rabbit dermal fibroblasts by 92%; a similar reduction in CTGF protein was confirmed by Western blot (data not shown). A scrambled mismatch control 20-mer that contained a random mix of all four bases was used as a control to assess specificity of the phosphorothioate oligodeoxynucleotide.

For injection in vivo, 50 mg of the antisense or scramble oligonucleotide was dissolved in 1.5 ml of sterile phosphate-buffered saline. This stock solution was then further diluted to provide a final concentration of 3 mg/ml of oligonucleotide. Based on prior work using antisense oligonucleotides in this model, (Sisco et al. 2005) 300 micrograms of antisense oligonucleotides were injected into each wound at each time point.

Rabbit Wound and Scar Models

This study used two different models that have been validated separately. The wound healing model employs a 6-mm wound, which was found to heal predictably over 1-2 weeks. The scar model relies on a 7-mm wound; the larger diameter of this wound leads to significantly more scar hypertrophy than is seen in the 6-mm wounds. This rabbit model of hypertrophic scarring has several similarities to human hypertrophic scars. (Morris et al. 1997) The scars are palpable and persist for up to nine months. Their microscopic appearance is similar to that found in humans; histology demonstrates irregularly arranged collagen fibers and increased vascularity. Like human scars, they respond to steroid injections and to topical silicone treatment (Morris et al. 1997; Saulis et al. 2002) and are less prominent in aged animals. (Marcus et al. 2000) Application of neutralizing antibodies to TGF-β reduces scar hypertrophy (Lu et al. 2005).

For the purposes of this study, all animals were housed under standard conditions and treated according to an experimental protocol approved by the Animal Care and Use Committee of Northwestern University. For all procedures, rabbits were anesthetized with intramuscular ketamine (60 mg/kg) and xylazine (5 mg/kg). After tissue harvest, previously anesthetized animals were euthanized with an intracardiac injection of pentobarbital (200 mg/kg).

Four circular punch wounds were made on the ears of white New Zealand rabbits as previously described. (Mustoe et al. 1991) These wounds were made to the level of the ear cartilage using an operating microscope. Per applicants' standard methodology, six-millimeter wounds were created to assess early wound healing kinetics in the wound-healing cohort. To evaluate scar hypertrophy, seven-millimeter wounds were created. Each wound was dressed with a sterile occlusive dressing (Tegaderm, 3M, St. Paul, Minn.). Dressings were kept in place or replaced as needed until gross wound closure had occurred or the wound was harvested, whichever came first. Wounds that exhibited signs of desiccation, necrosis, or infection were excluded. Less than five percent of the wounds were excluded; these were evenly distributed among treatment groups. This rate was consistent with untreated versions of the models Wound and Scar Treatment Antisense oligonucleotides were injected intra-dermally using a 29-gauge needle. When treatment was performed prior to wounding, a 150 µl wheal was raised where the wound was planned one hour prior to surgery. Treatment of existing wounds was performed with six equal intra-dermal injections (17 µl each) into the periphery of each healing wound. To validate the injection process and to evaluate the in vivo durability of the oligonucleotides, 6-mm wounds in two rabbits were injected with 150 µg of a 2'-O-methoxyethyl modified oligonucleotide one hour prior to wounding. These wounds were harvested at days 2, 4, 6, and 8. Oligonucleotide distribution was determined using immunohistochemistry of wound sections from oligonucleotide injected and vehicle-injected wounds, as described previously, using a proprietary monoclonal antibody that specifically recognizes this class of antisense. (Butler et al. 1997)

Wound Cohorts

To assess whether antisense blockade of CTGF affects wound repair, 6-mm wounds were made in the ears of six rabbits. These wounds were treated with anti-CTGF or scrambled oligonucleotides one hour prior to wounding and at post-wounding days 3 and 6. Wounds were photographed at days 7 and 10 and were harvested at day 10 for histological analysis.

Three cohorts of rabbits were used to evaluate whether blockade of CTGF affects hypertrophic scarring. The control group, which consisted of 12 rabbits with four 7-mm wounds on each ear, was used to determine the temporal expression of CTGF during scar development. Wounds from three rabbits were harvested at each time point (days 7, 14, 28, and 40) for histology and mRNA analysis. Six rabbits, with four 7-mm wounds on each ear, comprised the early scar treatment cohort. These wounds were treated with anti-CTGF or scramble oligonucleotides one hour prior to wounding (day 0) and at post-wounding days 5 and 10. The late scar treatment cohort, consisting of 12 rabbits, was treated with anti-CTGF or scramble oligonucleotides on post-wounding days 14, 19, and 24. Total RNA was extracted from scars in the late treatment cohort and RT-PCR was performed as described below to confirm a reduction in CTGF mRNA expression and to determine levels of types I and III collagen, fibronectin, and TIMP-1.

Histology

Figure 6:
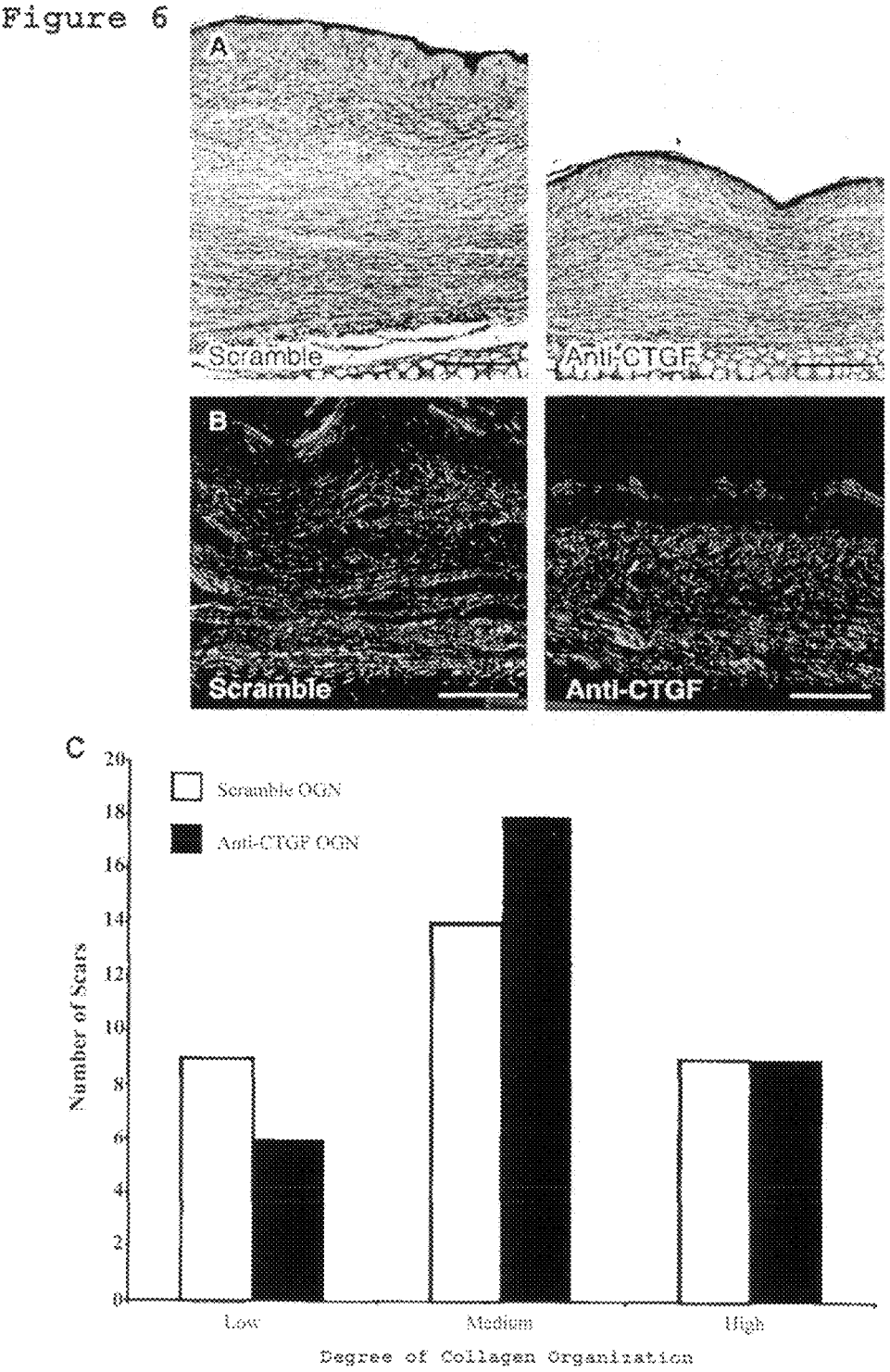
FIG. 6C shows that there was no statistical difference in collagen organization between scramble and anti-CTGF ASO-treated wounds at day 28 post-wounding. Photographs of representative sections of dermis stained with trichrome and sirius red are shown in FIGS. 6A and 6B, respectively. The scale bar is 0.25 mm.

Five micrometer wound and scar sections were stained with hematoxylin and eosin for quantification of wound epithelialization, granulation tissue deposition, and scar hypertrophy, as previously described, using a digital image analysis system (NIS-Elements Basic Research, Nikon Instech Co, Kanagawa, Japan). (Lu et al. 2005) Scar hypertrophy was measured using the scar elevation index (SEI), a ratio of cross-sectional scar area to the area of tissue excised to make the wound (FIG. 6d). Sections were stained using Masson's trichrome and sirius red to evaluate collagen organization within the scar, which was graded under 40× magnifications as low, medium, or high. Two observers blinded to treatment evaluated each section.

Immunochemistry

Primary antibodies used included goat anti-human CTGF (from Dr. Gary Grotendorst, Lovelace Resp Res Institute, Albuquerque, N. Mex.), mouse anti-human CD31 antibody (Dako North America, Inc., Carpinteria, Calif.), and the α-SMA immunostaining kit (Sigma, St. Louis, Mo.). Antigen retrieval was performed for α-SMA and CD31 staining by boiling the sections in antigen retrieval buffer (Dako NA) for 15 or 60 minutes, respectively.

The slides were incubated with the primary antibodies directed against either CTGF (1:150), CD31 (1:10), or α-SMA. CD31 and α-SMA slides were then incubated with biotinylated secondary anti-mouse antibody (Sigma). CTGF slides were incubated with biotinylated rabbit anti-goat antibody (1:100; Vector Laboratories, Inc., Burlingame, Calif.). Detection of the antibody complex was performed with ExtrAvidin-Peroxidase (CD31 and α-SMA) or avidin-biotin complex (CTGF) and DAB (Vector Laboratories, Inc.). Wounds injected with the reporter oligonucleotide were stained using a monoclonal antibody as previously described. (Butler et al. 1997)

Inflammatory cells were counted manually (based on morphology) in four high-power fields by two observers blinded to the treatment group. For digital analysis, brightfield images were acquired using the Nikon system. Images were converted to a monochromatic channel and a threshold was set for each stain, enabling automated DAB quantitation. The same threshold was used for each section of a given stain. Tiling of the digital images allowed for analysis of each scar in its entirety.

Blood vessel lumens in CD31-stained sections within scars were automatically counted using this threshold. Likewise, the density of α-SMA and CTGF staining within the scars was analyzed digitally and is expressed as a percentage of the total scar area.

Real-Time PCR

The epidermis and dermis on the unwounded side of the ear were sharply excised from each frozen specimen. The tissue was disrupted and homogenized in a Mini-Beadbeater bead mill (Biospec Products, Inc., Bartlesville, Okla.) in guanidine thiocyanate-based lysis buffer (RLT buffer, Qiagen). Total RNA was extracted using the column-based RNeasy mini kit (Qiagen) per the manufacturer's protocol. On-column DNA digestion was performed using the RNase-free DNase Set (Qiagen) to prevent genomic DNA carryover. First-strand cDNA was created from 1 μg total RNA using the High Capacity cDNA Archive Kit (Applied Biosystems, Inc., Foster, Calif.) using random hexamer primers per manufacturer instructions. PCR primers and probes (Table 1) were designed based on GenBank sequence data for CTGF, collagen I-a2, collagen IIIa1, fibronectin, and tissue inhibitor of metalloproteinase-1 (TIMP-1). The 5' ends of the reporter probes were labeled with 6-FAM (carboxyfluorescein); the 3' ends were labeled with TAMRA (6-carboxy-tetramethyl-rhodamine). Prior to use, each primer set was evaluated to ensure acceptable efficiency and specific binding. Commercially available primers for 18S rRNA, labeled with a VIC probe (Applied Biosystems) were used as an endogenous control. mRNA expression was measured in triplicate using real-time multiplex PCR on an ABI Prism 7000 Sequence Detection System (Applied Biosystems). Each PCR reaction included 1 μl cDNA template (10 ng total RNA), 900 nM target primers, and 1.25 μl 18S primers in a final reaction volume of 25 μl. Cycling parameters were as follows: 50° C. (2 min), 95° C. (10 min), and 40 cycles of 95° C. (15 sec) and 60° C. (1 min). No-template controls were run to exclude amplification of genomic DNA. The fluorescence curves of the PCR products were evaluated using ABI Prism 7000 SDS Study software (Applied Biosystems) to yield relative expression data.

TABLE 1

Oligonucleotide primer and probe sequences used for real-time RT-PCR

| Gene | Sequence |
|---|---|
| CTGF | Forward: 5'-AGCCGCCTCTGCATGGT-3'<br>Reverse: 5'-CACTTCTTGCCCTTCTTAATGTTCT-3'<br>Probe: 5'-AGGCCTTGCGAAGCTGACCTGGA-3' |
| Col Ia2 | Forward: 5'-TTCTGCAGGGCTCCAATGAT-3'<br>Reverse: 5'-TCGACAAGAACAGTGTAAGTGAACCT-3'<br>Probe: 5'-TTGAACTTGTTGCCGAGGGCAACAG-3' |
| Col IIIa1 | Forward: 5'-CCTGAAGCCCCAGCAGAAA-3'<br>Reverse: 5'-AACAGAAATTTAGTTGGTCACTTGTACTG-3'<br>Probe: 5'-TTGCACATTTTATATGTGTTCCTTTTGTTCTAATCTTGTC-3' |
| TIMP-1 | Forward: 5'-CGCAGCGAGGAGTTTCTCA-3'<br>Reverse: 5'-GCAAGTCGTGATGTGCAAGAG-3'<br>Probe: 5'-CGCTGGACAACTGCGGAACGG-3' |
| Fn | Forward: 5'-CACCCCAGAGGAAGAAACATG-3'<br>Reverse: 5'-AAGACAGGGTCTGCCAACGT-3'<br>Probe: 5'-CTCTGCAAAGGTCCATCCCAACTGGA-3' |
| 18S | Forward: 5'-GCCGCTAGAGGTGAAATTCTTG-3'<br>Reverse: 5'-CATTCTTGGCAAATGCTTTCG-3'<br>Probe: 5'-ACCGGCGCAAGACGGACCAG-3' |

Statistical Analysis

Data were analyzed using Prism software (GraphPad Software, Inc., San Diego, Calif.). Comparisons of SEI and gene expression among scramble and treatment groups were performed using the Student's t-test. Comparisons of more than two groups were performed using one-way analysis of variance with Bonferroni testing based on our experimental protocol. Differences in collagen organization were evaluated using chi square bivariate tabular analysis. A P-value of less than 0.05 was considered to be statistically significant.

Results

CTGF Demonstrates Progressive Up-Regulation During Scar Formation

An objective of this study is to observe the temporal expression of CTGF in a rabbit ear hypertrophic scar model and compare this pattern to its expression during normal wound healing. Levels of CTGF mRNA were negligible in unwounded skin; its expression in healing dermal ulcers continued to rise steadily through day 40 (FIG. 1). This contrasts with a prior report in a dead-space chamber model of granulation tissue deposition, (Igarashi et al. 1993) in which CTGF expression peaked between days 6-9 and then returned to baseline. Previously, this model shows that TGF-β1 and TGF-β2 peak near day 7 and between days 14-28, respectively. (Kryger et al. 2007) The fact that CTGF is expressed at high levels during late scarring in this model implies that it may augment the heightened deposition of extracellular matrix that continues through day 40 or in the remodeling of matrix at this relatively late time point. It further implies that the high level of CTGF expression at day 40 is independent of TGF-β1 or TGF-β2, suggesting an alternative regulatory pathway.

Injected Oligonucleotides are Durable in a Rabbit Model of Wound Healing

The sensitivity of antisense oligonucleotides to degradation by nucleases in vivo has largely been overcome by the development of a 2'-O-methoxyethyl chemical modification. (Zhang et al. 2000) However, wounds have a heterogeneous population of cells that migrate, divide, and release a variety of enzymes that could dilute or degrade the effectiveness of nucleic acids. Therefore, to evaluate the durability and uptake of the 2'-O-methoxyethyl oligonucleotides in this model, the distribution and durability of an oligonucleotide in the skin was monitored using a monoclonal antibody that specifically recognizes certain oligonucleotide sequences. (Butler et al. 1997) Immunohistochemistry demonstrated intracellular retention of injected oligonucleotide within and adjacent to the wound at days 2, 4, 6, and 8 post-wounding. The oligonucleotide was not found in unwounded skin on the opposite side of the ear.

Antisense Oligonucleotides to CTGF are Bioactive In Vivo

RT-PCR was used to measure CTGF mRNA and immunohistochemistry to measure CTGF protein following treatment with anti-CTGF oligonucleotides in the late treatment cohort (treated on days 14, 19, and 24; harvested on day 28). At the time of harvest, the level of CTGF mRNA in the antisense-treated scars was reduced by 55% ($P<0.05$) compared to scramble-oligonucleotide treated scars (FIG. 2A). Digital analysis of sections stained for CTGF revealed a reduction in CTGF staining among antisense-treated wounds (FIGS. 2B, 2C and 2D). The difference in efficacy we observed between the oligonucleotide in vitro (92% reduction in mRNA) versus in vivo underscores the differences between cell culture and animal pharmacology. It likely reflects different uptake mechanisms when cationic lipids are used in monolayer culture, as well as the heterogeneous nature of the cell population in vivo.

Inhibition of CTGF Signaling Does not Significantly Affect Early Wound Closure

Figure 4:
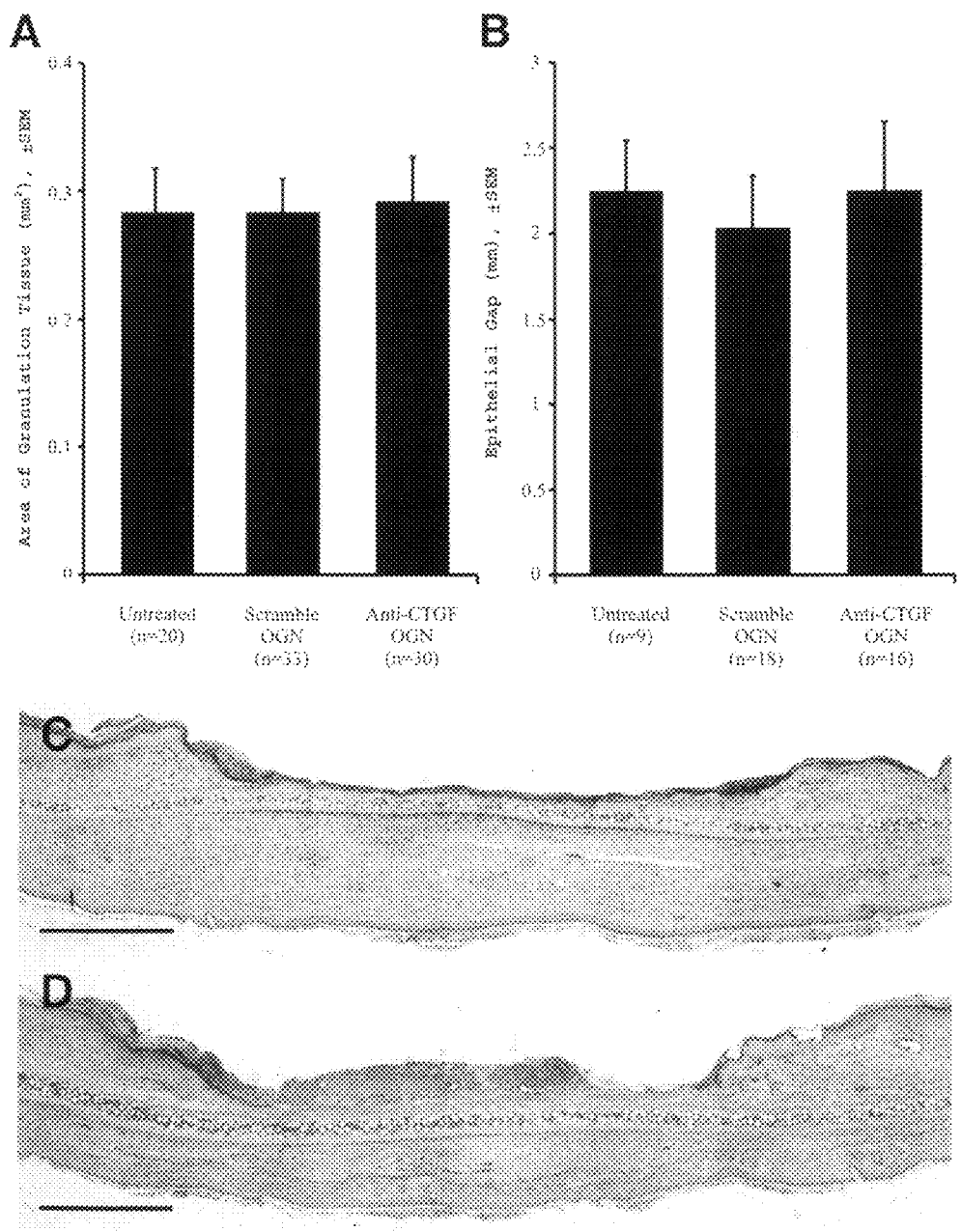
FIG. 4 shows that histologic measures of wound healing are similar in antisense- and scramble-treated wounds.

Prior investigations have demonstrated that oligonucleotide-mediated blockade of TGF-β1 and TGF-β2 delays the deposition of granulation tissue in this model. (Sisco et al. 2005) Given that CTGF mediates many of the proliferative and matrix-related effects of TGF-β1 or TGF-β2, the study sought to determine whether CTGF is necessary for normal healing. (Mustoe et al. 1991) Injection of anti-CTGF oligonucleotides at the time of wounding and at day 3 did not have a significant impact on wound healing. Gross wound closure, as measured histomorphometrically, was unaffected at days 7 and 10 (FIG. 3). The cross-sectional area of granulation tissue in the wound was not different between anti-CTGF-oligonucleotide-treated, scramble-oligonucleotide-treated, and untreated wounds ($0.29\pm0.03$ vs. $0.28\pm0.03$ mm$^2$ vs. $0.28\pm0.04$ mm$^2$) (FIG. 4A). The gap between the leading edges of epithelium migrating into the wound was likewise similar between treatment groups ($2.2\pm0.4$ mm vs. $2.0\pm0.3$ mm vs. $2.2\pm0.3$ mm, respectively) (FIG. 4B). FIG. 4C shows a representative scramble control ASO treated wound at day 10. FIG. 4D shows a representative anti-CTGF-ASO treated wound at day 10. The scale bar is 1 mm. Hematoxylin and eosin stain was used in the sample preparation. These results clearly demonstrate that treatment with an ASO inhibitor of CTGF expression such as an ASO with the sequence in SEQ ID No. 1 or 2 has no effect on the early wound healing response subsequent to the generation of a wound, even though this treatment reduces subsequent severity of hypertrophic scarring. This was an unexpected and novel finding.

Early and Late Inhibition of CTGF Reduces Scar Hypertrophy

Figure 5:
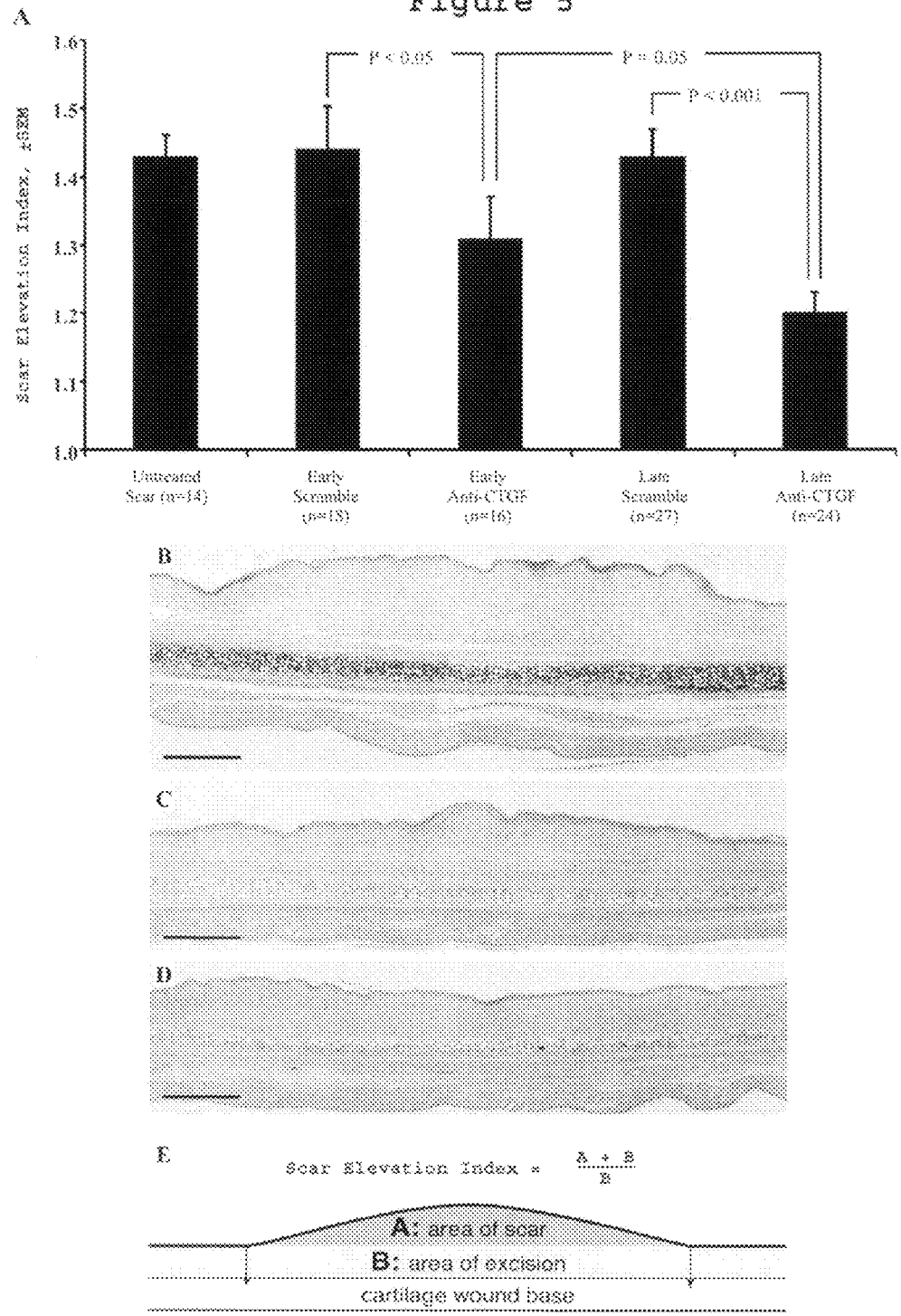

Prior experiments blocking TGF-β1 or TGF-β2 or procollagen C-proteinase have suggested that timing plays a critical role in determining attenuation of scarring; later treatments correlate with more efficacious reductions in scar hypertrophy. (Lu et al. 2005, Reid et al. 2006) As CTGF mRNA expression peaks later than TGF-β1 or TGFβ 2 in this model, it is postulated that late blockade of CTGF would have a more pronounced effect on scarring. FIG. 5A shows that early and late blockade of CTGF reduced scar hypertrophy. Unexpectedly, the data presented indicate that late dosing provides better responses compared to the response provided by early dosing. Early injection of wounds with 300 μg anti-CTGF oligonucleotides at days 0, 5, and 10 post-wounding reduced the scar elevation index (SEI) by 29% (FIG. 5C) compared to scrambled control oligonucleotide at day 28 ($p<0.05$) (FIG. 5B). Late injection of healing wounds, at days 14, 19, and 24, reduced scar elevation by 53% (FIG. 5D) in two separate cohorts of rabbits ($P<0.001$). The difference in scarring between the early and late treatment cohorts was statistically significant ($P=0.05$). FIGS. 5B to 5D are photographs of the specimens. FIG. 5E provides the formula for a scar elevation index (SEI) as a measure of the severity of the scarring.

Clinical experience with burns and work with various excisional models have suggested that a delay in epithelialization contributes to scar hypertrophy. (Mustoe et al. 2004) Keratinocytes play complex paracrine roles in fibroblast function and differentiation, and may down-regulate fibrotic processes. It takes up to twelve days to re-establish epithelial coverage of seven-millimeter wounds in this model; this contrasts with incisional models of healing, which, in the absence of tension, do not tend to result in significant scars. As described above, inhibition of CTGF did not affect epithelial closure in healing wounds or the amount of epithelium on the scars. As such, it seems unlikely that the effect we observed is indirectly mediated through an alteration in epithelial proliferation.

Blockade of CTGF Does Not Have a Measurable Impact on Angiogenesis, Inflammation, or Collagen Organization.

Blocking TGF-β1 or TGF-β2 (Shah et al. 1994) has been shown to alter the dermal architecture of healing incisional scars. In this study, however, there was no significant difference in collagen organization as evaluated with trichrome and sirius red staining (FIG. 6C). Photographs of representative sections of dermis showing trichrome and sirius red stains are shown in FIGS. 6A and 6B, respectively. Down-regulation of CTGF instead caused a reduction in the absolute amount of matrix deposited within the scars, which is in contrast to the changes in dermal architecture shown with TGF-β modulation. CD-31 immunostaining (data not shown) was used to evaluate angiogenesis and leukocyte infiltration. In this study, staining indicated a trend toward reduced angiogenesis in CTGF antisense treated scars; however, this finding was not statistically significant. There was minimal macrophage or neutrophilic presence in the wounds. No difference in the population of either of these cells was measurable, suggesting that a difference in inflammation was not the cause of the observed effects.

Figure 7:
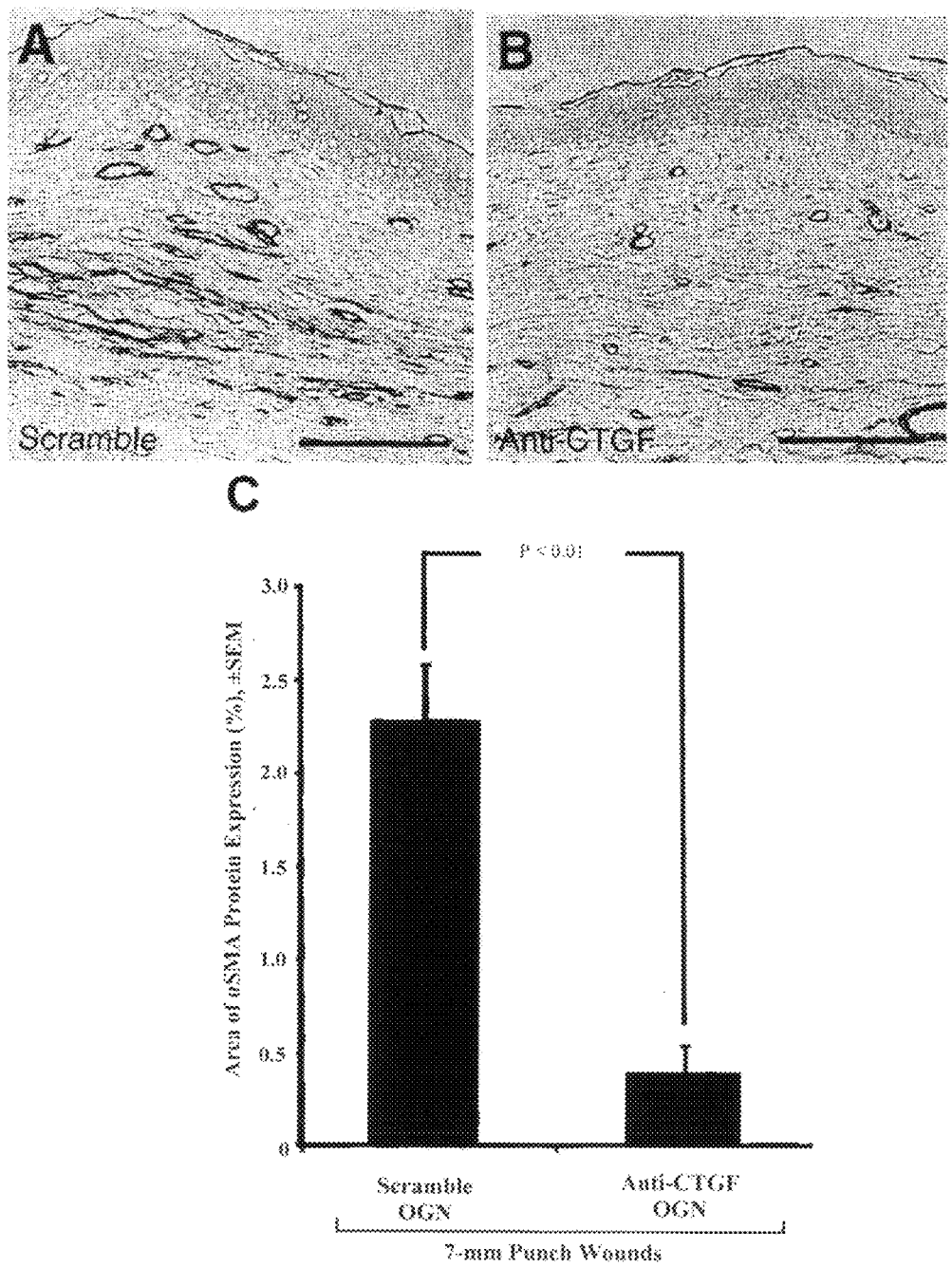
FIG. 7C shows that late inhibition of CTGF reduced the α-SMA-stained myofibroblast population in scars at day 28 post-wounding. Anti-α-SMA-antibody-stained sections were digitally analyzed for color density, which is expressed as percent staining relative to scar area. Representative sections of stained scramble and antisense-treated wounds are shown in FIGS. 7A and 7B, respectively. The scale bar is 0.25 mm.

Blockade of CTGF is Associated with a Marked Reduction in α-SMA-Positive Myofibroblasts In untreated scars, immunohistochemistry revealed significant staining for α-smooth muscle actin α-SMA), the most reliable marker for the myofibroblast phenotype. Myofibroblasts, which elaborate matrix proteins and initiate wound contraction, are transiently present in healing wounds; they normally disappear through apoptosis beginning at day 16. The persistent presence of myofibroblasts is a distinctive feature of hypertrophic scars and is thought to contribute to the excessive matrix production and contracture found therein. (Baur et al. 1975; Ehrlich et al. 1994) Along with TGF-β1 or TGF-β2, mechanical stress is required to generate α-SMA-positive myofibroblasts. This may explain the established surgical tenet that excessive wound tension leads to unfavorable scarring. (Arem et al. 1976) The wounds in this animal model do not contract since the wound is rigidly splinted by the underlying cartilaginous base. (Mustoe et al. 1991) As fibroblasts try to contract this wound they experience isometric stress, which provides the physical milieu necessary for myofibroblast differentiation. (Hinz et al. 2001; Tomasek et al. 2002) In this study, blocking CTGF at late time points markedly reduced the presence of α-SMA-expressing myofibroblasts in the scars despite the continued presence of tension in the wound (FIG. 7C). Anti-α-SMA-antibody-stained sections were digitally analyzed for color density, which is expressed as percent staining relative to scar area. Representative sections of stained scramble and antisense-treated wounds are shown in FIGS. 7A and 7B, respectively. This finding may explain part of the observed reduction in scar hypertrophy, as hypertrophic scar myofibroblasts contribute heavily to matrix elaboration. (Ghahary et al. 1993; Harrop et al. 1995)

Figure 8:
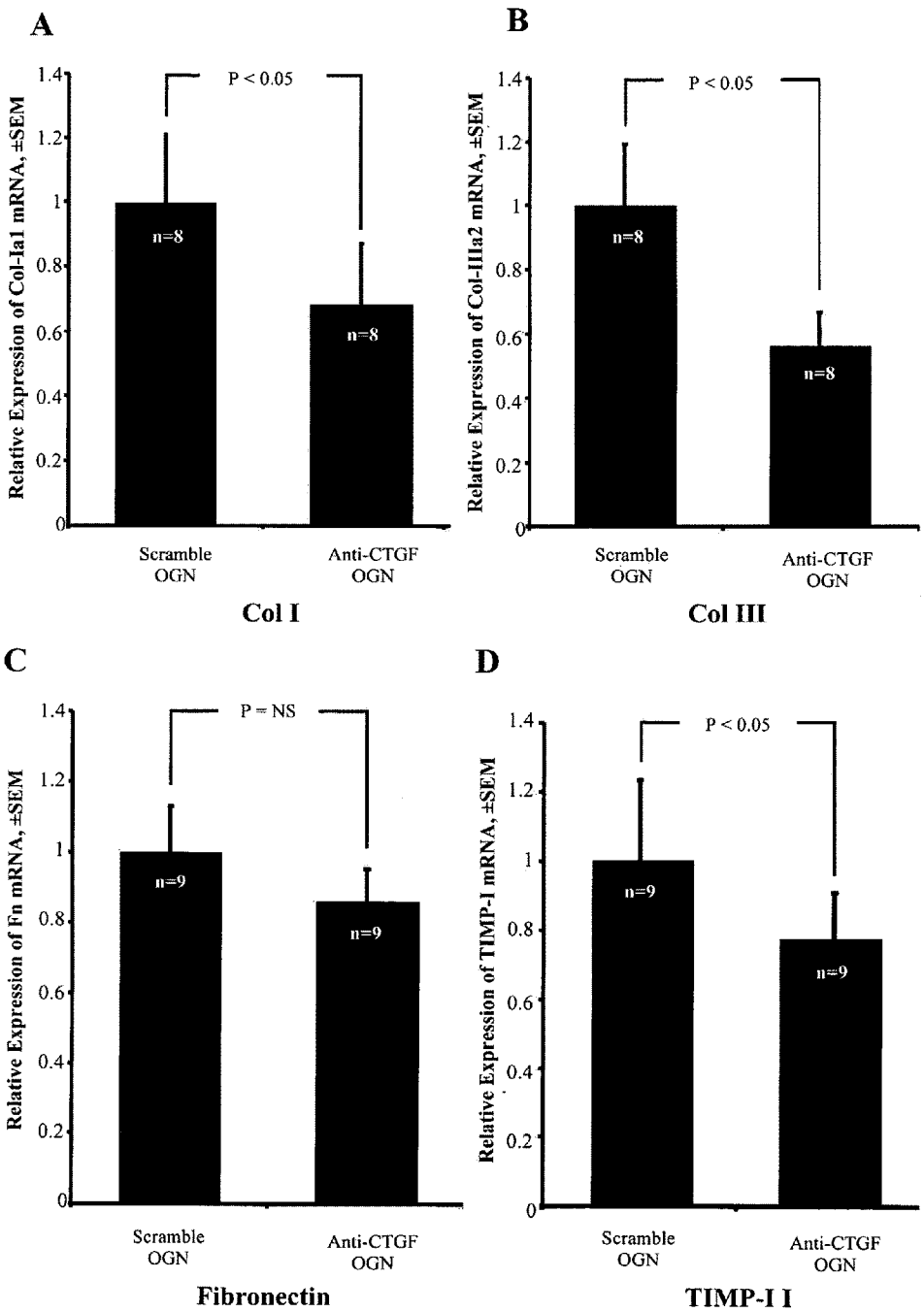
FIG. 8 presents graphical representations of the effect of ASO CTGF blockade as compared to an oligonucleotide control on Collagen Types I (FIG. 8A), Collagen Type III (FIG. 8B), Fibronectin (Fn) (FIG. 8C), and TIMP-1 expression (FIG. 8D) in vivo as measured by RT-PCR. Scars were treated with anti-CTGF oligonucleotides in the late treatment cohort on days 14, 19, and 24 and harvested on day 28.

Blockade of CTGF is Associated with Reductions in TIMP-1 and Types I and III Collagen Pathologic scarring results from excessive production and diminished degradation of ECM macromolecules. In order to evaluate the molecular effects of CTGF on matrix production, mRNA expression of collagen and fibronectin, which constitute the bulk of the scar ECM (FIG. 8A to C) were measured. As expected, collagen I expression was decreased by 31% (P<0.05) and type III collagen was reduced by 41% (P<0.05) in anti-CTGF-treated scars. Fibronectin expression was reduced by 14%; this was not statistically significant. Next, the expression of TIMP-1, which protects collagen and other matrix elements from degradation by metalloproteinases (FIG. 8D) were measured. SiRNA blockade of CTGF has been shown to reduce TIMP-1 expression in vitro. (Li et al. 2006) Similarly, the results indicated that TIMP-1 mRNA expression decreased by 23% in anti-CTGF treated scars (P<0.05). There was no detectable difference in the levels of collagen, fibronectin, and TIMP-1 in the early treatment cohort. This is presumably because these wounds were harvested 18 days after the last antisense treatment, at which point the oligonucleotide was unable to effect a measurable difference in downstream gene expression.

Discussion

This study assesses the importance of CTGF to wound repair and hypertrophic scarring and evaluate its suitability as a target for anti-scarring therapies. The data demonstrate that modified antisense oligonucleotides against CTGF reduce hypertrophic scarring in an animal model. The data also show that blocking CTGF does not have a measurable impact on the deposition of granulation tissue formation or epithelialization, this lack of effect on wound healing was both unexpected and will be highly beneficial in a clinical setting, where a reduction in wound healing would not be desired. The reduction in scarring that was observed is associated with a decrease in myofibroblast presence in the scars and a reduction in genes associated with matrix production and the prevention of matrix degradation. These results support the hypothesis that CTGF is an important mediator of hypertrophic scarring and shed light on its role in scar pathogenesis.

Many of the findings corroborate the clinical and in vitro observations that have been published previously. High levels of CTGF are transiently present in acute wounds. (Lin et al, 2005; Igarashi et al. 1993, Dammeier et al., 1998) In our hypertrophic scarring model, CTGF mRNA expression continues to rise through day 40 post-wounding and parallels the progressive hypertrophy of scars at these time points. This continued CTGF expression outlasts the elevated expression of TGF-β1 or TGF-β2. (Kryger et al. 2007) It correlates with cell-culture data from hypertrophic scar fibroblasts (Colwell et al. 2005) and mirrors observations from several fibrotic disorders such as scleroderma.

Prolonged expression of CTGF is likely to contribute to the excessive accumulation of matrix that results in scar elevation in this model. CTGF auto-induction may contribute to high levels of CTGF in the absence of TGF-β1 or TGF-β2. (Riser et al. 2000) Moreover, there is accumulating evidence that mechanical stress is an important and independent inducer of CTGF expression. (Garrett et al, 2004; Kessler et al. 2001; Schild et al. 2002; Chaqou et al. 2006) This model, in which the wound is prevented from contracting by the cartilaginous base, is a rigid model of healing. The isometric tension generated in fibroblasts as they attempt to contract the wound may explain the elevated levels of CTGF expression and the excessive accumulation of matrix that results.

A wealth of observational data has fueled speculation that CTGF is an important mediator of wound healing: there is augmented expression of CTGF in healing wounds; CTGF enhances the production of many proteins that are essential to healing; and CTGF knockout mice exhibit defects in matrix production and remodeling during embryogenesis. (Ivkovic et al. 2003) However, the importance of CTGF to wound healing has not been established in vivo. This study unexpectedly demonstrates that antisense inhibition of CTGF mRNA during and soon after injury does not have a measurable impact on two parameters of healing. The migration of epithelium across acute wounds and the thickness of the epithelium in mature scars were unchanged by CTGF blockade.

Although CTGF is known to participate in granulation tissue formation when injected, (Frazier et al, 1996; Mori et al. 1999) its inhibition here did not affect the production of granulation tissue. These results suggest that normal CTGF expression may not be necessary to the regenerative capacity of the acute wound. It is possible that the antisense oligonucleotide did not block CTGF sufficiently to unmask a subtle role in healing. However, the data clearly demonstrated that there is a therapeutic window in which CTGF-related scar hypertrophy can be blocked without having a detrimental effect on healing.

The corollary question to evaluating the importance of CTGF to wound healing is whether CTGF plays an important role in scar formation. While several reports have shown an ability to reduce tissue fibrosis by blocking CTGF signal transduction in vivo, the effect of modulating CTGF on dermal scar formation has not been explored. The most important finding here is that antisense oligonucleotides to CTGF cause a significant reduction in hypertrophic scarring. Late administration of antisense oligonucleotides to CTGF reduces scar elevation more than does early administration. This is accompanied by reduced expression of type I collagen, type III collagen, and TIMP-1, all of which are known to be induced by CTGF.

The degree of scar reduction was proportional to the level of CTGF mRNA expression at the time of oligonucleotide administration. These findings establish that excessive CTGF mRNA expression is responsible for at least a portion of the hypertrophic scar phenotype we observed. This clinical effect is significant given that we were unable to achieve the same degree of transcript reduction in vivo as in vitro. Naked antisense oligonucleotides are known to be internalized into multiple cells in animals after systemic administration. (Butler et al., 1997) In this study, the difficulty reflects the complexity of the healing wound, in which there is a heterogeneous population of transiently appearing cells. It also demonstrates challenges inherent to reducing gene expression in wounds. Methods to improve transfection of oligonucleotides might further reduce CTGF levels and may further highlight its importance to scarring.

In this study, blocking CTGF was associated with a marked reduction in the presence of α-SMA-expressing myofibroblasts. Several cell-culture studies have implicated CTGF in myofibroblast differentiation. CTGF has been shown to mediate the effect of TGF-β on corneal fibroblast differentiation. (Garrett et al. 2004; Grotendorst et al. 2004) However, CTGF alone appears to be insufficient to induce α-SMA expression. (Folger et al. 2001) This has led to the hypothesis that mechanically-stressed fibroblasts become responsive to CTGF after being primed by TGF-β. (Garrett et al, 2004) Results of the applicants' experiment suggest that CTGF may orchestrate myofibroblast differentiation within or recruitment to hypertrophic scars. This provides an additional potential mechanism whereby targeting CTGF exerts its effect: through blockade of CTGF-mediated myofibroblast differentiation, which in turn manifests as reduced ECM production.

The importance of proper timing to effect the pharmacologic therapy of scars was previously noted in Lu et al. (2005). As with blocking TGF-β1 or TGFβ 2, the effects of blocking CTGF were more pronounced at later time points. This may simply reflect the increased expression of CTGF after day 14 post-wounding. If hypertrophic scarring results from sustained CTGF expression after TGF-β1 or TGF-β2 has started to decline, it seems logical that targeting it during its peak in expression will result in the most pronounced clinical result. Alternatively, the improved efficacy of late treatment may reflect the chronology of myofibroblast differentiation, which peaks in normal wounds at day 16. If CTGF coordinates myofibroblast recruitment, differentiation, or function, blocking it at this time point would presumably be most effective.

In spite of the circumstantial evidence implicating CTGF in dermal wound healing and scarring, its importance to these processes in vivo has not been well defined until the present setting. The data confirm that CTGF expression is sustained at high levels during scarring—after levels of TGF-β1 or TGF-β2 have returned toward baseline. It also further demonstrates that CTGF antisense oligonucleotide treatment effectively reduces scarring without having a deleterious effect on healing. This study identifies two mechanisms whereby CTGF may promote hypertrophic scarring: by augmenting or maintaining the persistence of α-SMA-positive myofibroblasts in the scar and by promoting the deposition of ECM through transcription of genes such as collagen and TIMP-1. One can envision a cycle, initiated by TGF-β1 or TGF-β2, whereby mechanical strain induces CTGF expression. CTGF enhances myofibroblast differentiation and elaboration of matrix macromolecules. These activated myofibroblasts then elaborate more CTGF. It is tempting to speculate that CTGF might provide a target by which this cycle might be broken. Since CTGF is a downstream regulator of collagen synthesis without the protean effects of TGF-β1 or TGF-β2, it may prove to be a more attractive target than TGF-β1 or TGF-β2 in modulating scarring.

Example 2

Antisense Inhibition of Connective Tissue Growth Factors (CTGF/CCN2) mRNA Limits Hypertrophic Scarring Combined Experiment Materials and Methods
Creating Wounds Four circular punch wounds were made on the ears of white New Zealand rabbits as previously described. These wounds were made to the level of the ear cartilage. An operating microscope was used to ensure complete removal of the epidermis, dermis, and perichondrium from each wound, such that a cartilage-based ulcer remained. six-millimeter wounds were created to assess early wound healing kinetics in the wound-healing cohort. Seven-millimeter wounds were created to evaluate scar hypertrophy in the scar cohort. Each wound was individually dressed with a sterile occlusive dressing (Tegaderm, 3M, St. Paul, Minn.) in order to prevent desiccation and cartilage necrosis. The integrity of the dressings and the condition of the wounds were checked daily.

Administering ASO

Figure 9:
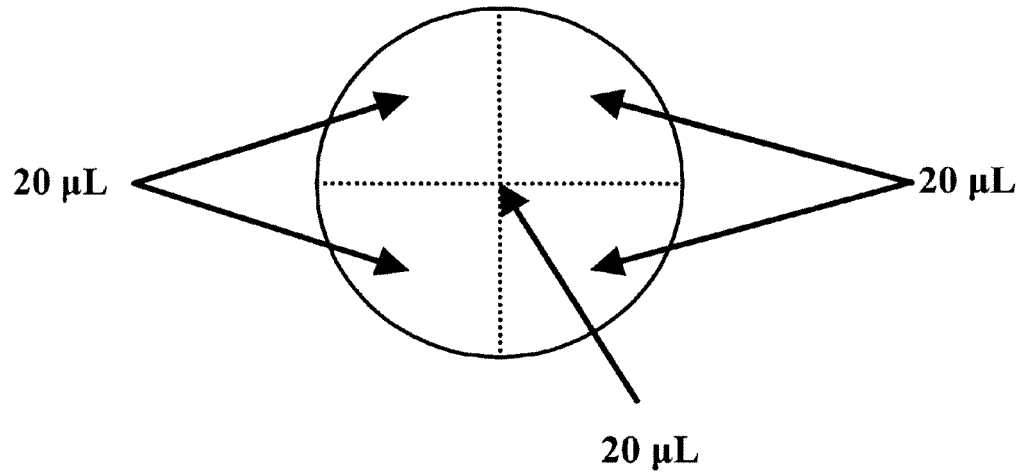
FIG. 9 shows a schematic of the injection sites of the circular ear wound consisting of five injections at 20 µL per injection for a total volume of 100 µL per wound.

Antisense oligonucleotides were injected intra-dermally using a 29-gauge needle on a 0.5 ml syringe. When treatment was performed prior to wounding, a 150 μl wheal was raised where the wound was planned one hour prior to surgery. Treatment of existing wounds was performed with six equal intra-dermal injections (17 μl each) into the periphery of each healing wound; or 4×20 μl injections with 20 μl in middle (FIG. 9).

Treatment Regime

The 6-mm wounds in two rabbits were injected with 150 μg of a 2'-Omethoxyethyl modified oligonucleotide one hour prior to wounding. To assess whether antisense blockade of CTGF affects wound repair, 6-mm wounds were made in the ears of six rabbits. These wounds were treated with anti-CTGF or scrambled oligonucleotides one hour prior to wounding and at post-wounding days 3 and 6. Wounds were photographed at days 7 and 10, and were harvested at day 10 for histological analysis.

Hypertrophic Scar

The animal model used in this experiment is the rabbit model of hypertrophic scarring that has several similarities to human hypertrophic scars. The scars are palpable and persist for up to nine months. Their microscopic appearance is similar to that found in humans; histology demonstrates irregularly arranged collagen fibers and increased vascularity. Like human scars, they respond to steroid injections and to topical silicone treatment and are less prominent in aged animals. To induce hypertrophic scarring, seven millimeter circular punch wounds were made on the ears of white New Zealand rabbits to the level of the ear cartilage using an operating microscope. Doses of 100 µg, 300 µg or 1000 µg of anti-CTGF oligonucleotide or scramble oligonucleotide were injected into the wound.

Figure 10:
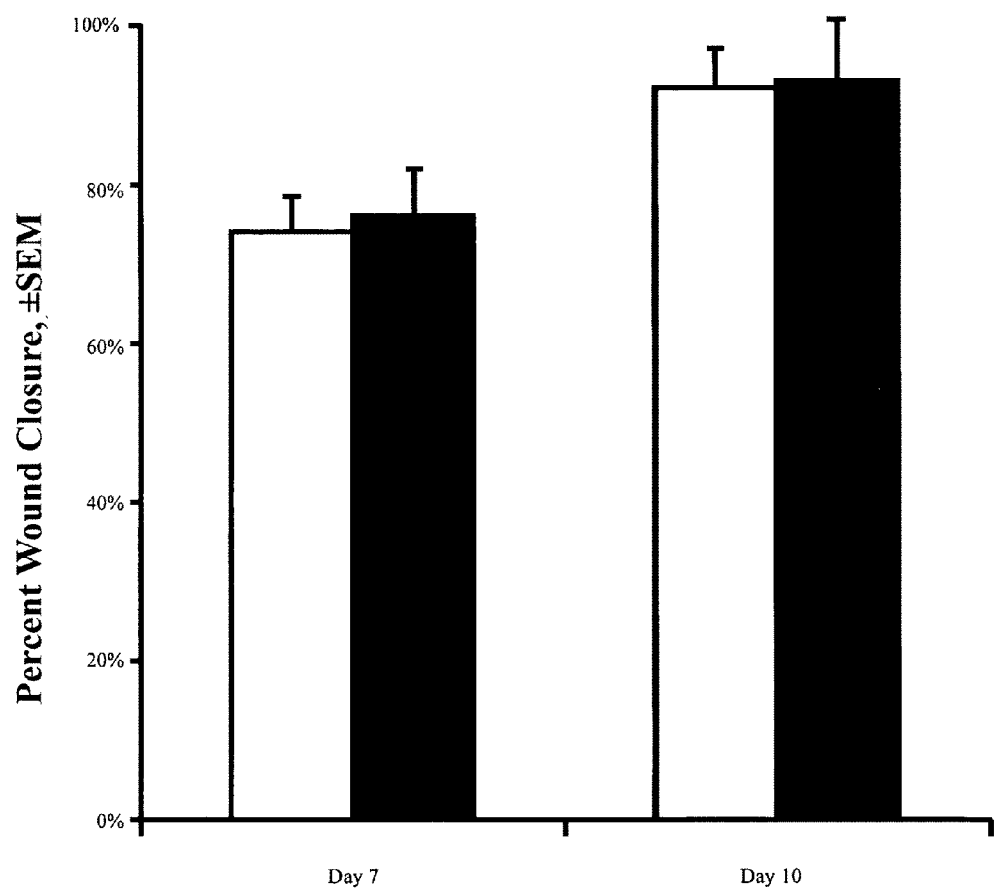
FIG. 10 shows that the percent wound closure, i.e. early healing response associate with CTGF ASO blockade in wounded rabbits.

Early Treatment
  Wounds were treated with anti-CTGF or scramble oligonucleotides one hour prior to wounding (day 0) and at post-wounding days 5 and 10.
Late Treatment
  Scar treatment cohort, consisting of 12 rabbits, was treated with anti-CTGF or scramble oligonucleotides on post-wounding days 14, 19, and 24. Dose response was observed. The preliminary conclusion is that 100 µg is sub-therapeutic, 300 µg indicates dose response, and 1000 µg indicates a better response than 300 µg.
Key Experiments Performed
  Key experiments performed in two cohorts are listed below:
  Cohort 1: 7 mm hypertrophic scar model (n=14 total)
  Reporter osteoglycin (OGN) was injected and harvested at days 2, 4, 8 for immunohistochemistry (IHC).
  Anti-CTGF injected at days 0, 3, harvested at day 7
  Anti-CTGF injected at days 0, 5, 10 or days 14, 19, 24; both harvested at day 28
  Photometric and histologic analyses of healing performed at days 7 and 10
  Scar evaluation index (SEI) calculated at day 28 (Refer to FIG. 5E for the formula to calculating the SEI to determine the severity of the hypertrophic scarring.)
  CTGF cloned; RT-PCR performed at days 7, 14, 28, 40 and after 1-5 days post-OGN injection
  Cohort 2: 7 mm hypertrophic scar model (n=17 total)
  CTGF expression determined at various timepoints in healing
  Antisense OGN tested for durability and bioactivity in vitro and in vivo
  Anti-CTGF or scramble injected early to assess wound healing
  Anti-CTGF or scramble injected early of late to assess scarring
Summary of Combination Experiment
  The first three groups were kept unchanged. For group four (both subgroups) a different dosing regime was used as follows:
  Day 14, 19, 24 dosed with CTGF ASO (SEQ ID No. 1 or 2) (at 300 µg in 100 µl)
  Day 15, 20, 25 dosed with TGFβ1 ASO (SEQ ID No. 3) (at 300 µg in 100 µl)
Results and Discussion
  To assess whether antisense blockade of CTGF affects hypertrophic scarring three groups of rabbits were used. The control group, which consisted of 12 rabbits with four 7-mm wounds on each ear, was used to determine the temporal expression of CTGF during scar development.
  Wounds from three rabbits were harvested at each time point (days 7, 14, 28, and 40) for histology and mRNA analysis. Six rabbits, with four 7-mm wounds on each ear, comprised the early scar treatment cohort. Photometric and histologic analyses of healing were performed at days 7 and 10. FIG. 10 shows the percent wound closure, i.e. early healing response associated with CTGF ASO blockade in wounded rabbits. These wounds were treated with anti-CTGF or scramble oligonucleotides one hour prior to wounding (day 0) and at post-wounding days 5 and 10. The late scar treatment cohort, consisting of 12 rabbits, was treated with anti-CTGF or scramble oligonucleotides on post-wounding days 14, 19, and 24.

Figure 11:
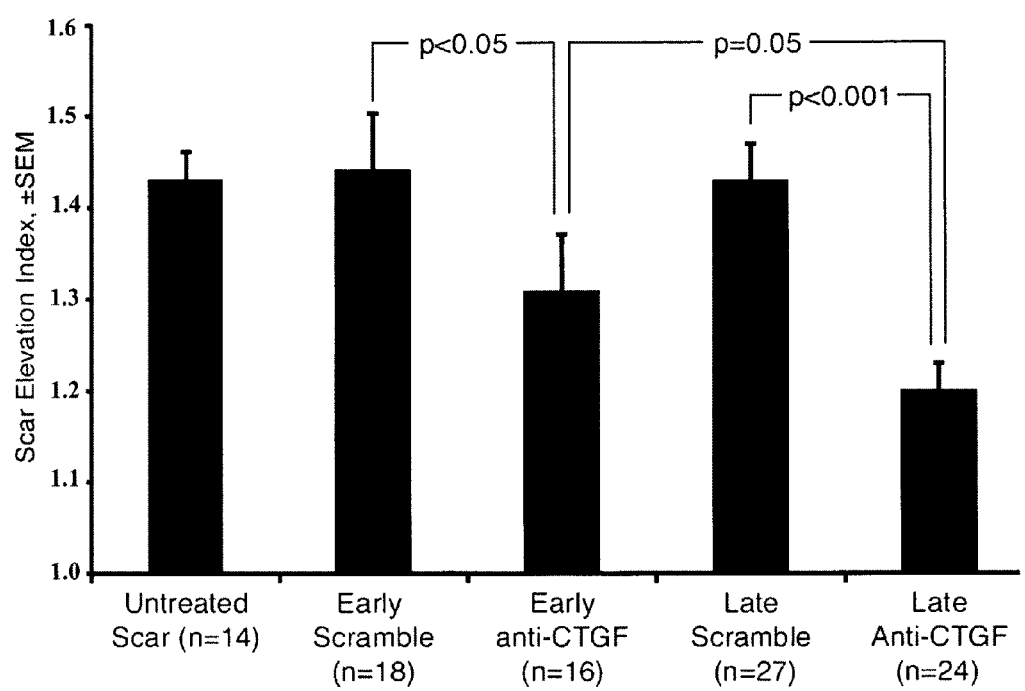
FIG. 11 shows the effect of various dose schedules, as measured by the scar elevation index (SEI), for the early and late dosed cohorts who received 300 µg doses. The data indicates that late dosing provides a better dose response as compare to the responses observed in the early dose group.

Injection of wounds with anti-CTGF oligonucleotides at days 0, 5, and 10 post-wounding reduced the scar elevation index (SEI) by 29% compared to scrambled control oligonucleotide at day 28 (p<0.05). Late injection of healing wounds, at days 14, 19, and 24, reduced scar elevation by 53% (FIG. 11) in two separate cohorts of rabbits (P<0.001). FIG. 11 shows the effect of these dose schedules, as measured by the scar elevation index, for the early and late dosing cohorts. The difference in scarring between the early and late treatment cohorts was statistically significant (P=0.05).

Figure 12:
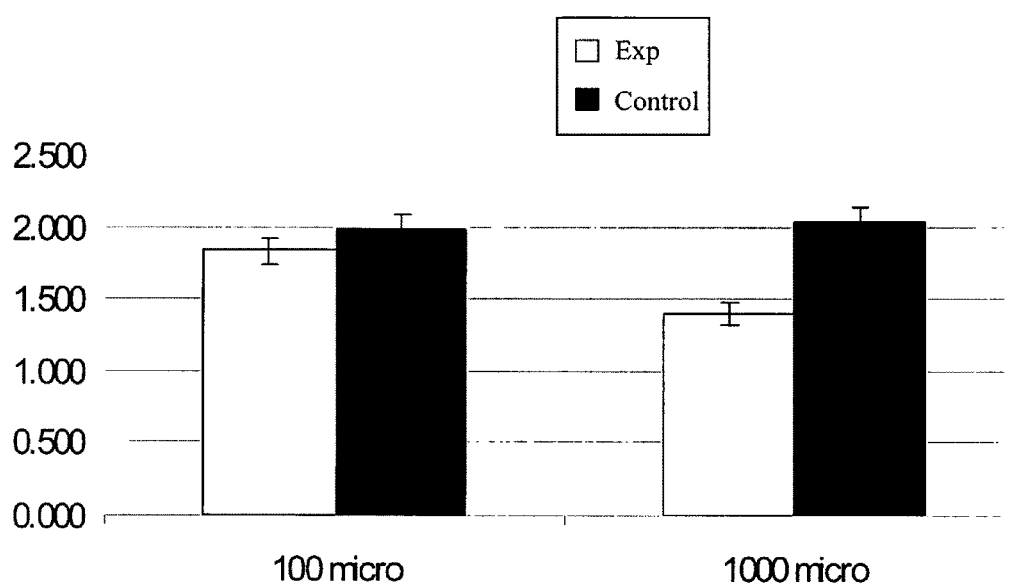
FIG. 12 shows the dose response for the late dosed cohort of rabbits receiving either 100 µg or 1000 µg dose as measured by the scar elevation index. The dose response shows more favorable reduction in hypertrophic scars in the 1000 µg dose group.

In a late dosed cohort of rabbits receiving either 100 µg or 1000 µg dose, the dose response as measured by the scar elevation index shows more favorable reduction of hypertrophic scars in the rabbits receiving 1000 µg dose than the 100 µg dose (FIG. 12).

Figure 13:
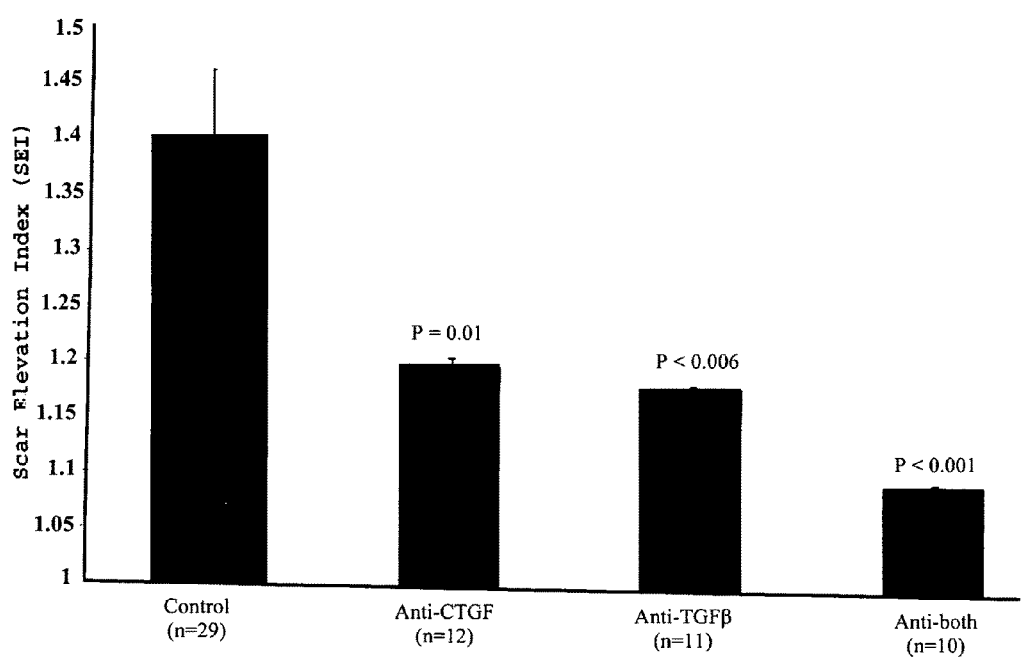
FIG. 13 shows that the late dosed cohort of rabbits receiving a combination of ASO to CTGF and ASO to TGFβ1 or TGFβ 2 at day 28 provides a particularly more favorable result in terms of reducing hypertrophic scars than the cohorts receiving either ASO to CTGF or ASO to TGFβ1 or TGFβ 2 alone.

In comparison, the late dosed cohort of rabbits receiving a combination of ASO to CTGF and ASO to TGF-β1 at day 28 provides a particularly more favorable result in terms of reducing hypertrophic scars than the cohorts receiving either ASO to CTGF or ASO to TGF-β1 (SEQ ID No:3) alone (FIG. 13). This was unexpected given the overlapping mechanisms of action of these two targets, and represents a novel finding.

These results demonstrate that 2'MOE-modified antisense oligonucleotides against CTGF reduce hypertrophic scarring in an animal model and blocking CTGF does not have a measurable impact on the deposition of granulation tissue formation or epithelialization. The reduction in scarring that was observed is associated with a decrease in myofibroblast presence in the scars and a reduction in genes associated with matrix production and the prevention of matrix degradation. These results support the hypothesis that CTGF is an important mediator of hypertrophic scarring and shed light on its role in scar pathogenesis.

REFERENCES

Abreu J G, Ketpura N I, Reversade B, De Robertis E M. Connective-tissue growth factor (CTGF) modulates cell signalling by BMP and TGF-beta. *Nat Cell Biol* 2002; 4(8):599-604.
Arem A J, Madden J W. Effects of stress on healing wounds: I. Intermittent noncyclical tension. *The Journal of surgical research* 1976; 20(2):93-102.
Baur P S, Larson D L, Stacey T R. The observation of myofibroblasts in hypertrophic scars. *Surg Gynecol Obstet* 1975; 141(1):22-6.
Blalock T D, Duncan M R, Varela J C, Goldstein M H, Tuli S S, Grotendorst G R, et al. Connective tissue growth factor expression and action in human corneal fibroblast cultures and rat corneas after photorefractive keratectomy. *Invest Ophthalmol Vis Sci* 2003; 44(5):1879-87.
Bonniaud P, Margetts P J, Kolb M, Haberberger T, Kelly M, Robertson J, et al. Adenoviral gene transfer of connective tissue growth factor in the lung induces transient fibrosis. *Am J Respir Crit Care Med* 2003; 168(7):770-8.
Butler M, Stecker K, Bennett C F. Cellular distribution of phosphorothioate oligodeoxynucleotides in normal rodent tissues. *Lab Invest* 1997; 77(4):379-88.
Chaqour B, Yang R, Sha Q. Mechanical stretch modulates the promoter activity of the profibrotic factor CCN2 through increased actin polymerization and NF-kappaB activation. *The Journal of biological chemistry* 2006; 281(29):20608-22.

Colwell A S, Krummel T M, Longaker M T, Lorenz H P. Fetal and adult fibroblasts have similar TGF-beta-mediated, Smad-dependent signaling pathways. *Plast Reconstr Surg* 2006; 117(7):2277-83.

Colwell A S, Phan T T, Kong W, Longaker M T, Lorenz P H. Hypertrophic scar fibroblasts have increased connective tissue growth factor expression after transforming growth factor-beta stimulation. *Plast Reconstr Surg* 2005; 116(5): 1387-90; discussion 91-2.

Dammeier J, Beer H D, Brauchle M, Werner S. Dexamethasone is a novel potent inducer of connective tissue growth factor expression. Implications for glucocorticoid therapy. *J Biol Chem* 1998; 273(29):18185-90.

Ehrlich H P, Desmouliere A, Diegelmann R F, Cohen I K, Compton C C, Garner W L, et al. Morphological and immunochemical differences between keloid and hypertrophic scar. *The American journal of pathology* 1994; 145(1):105-13.

Folger P A, Zekaria D, Grotendorst G, Masur S K. Transforming growth factor-betastimulated connective tissue growth factor expression during corneal myofibroblast differentiation. *Invest Ophthalmol Vis Sci* 2001; 42(11):2534-41.

Frazier K, Williams S, Kothapalli D, Klapper H, Grotendorst G R. Stimulation of fibroblast cell growth, matrix production, and granulation tissue formation by connective tissue growth factor. *J Invest Dermatol* 1996; 107(3):404-11.

Garrett Q, Khaw P T, Blalock T D, Schultz G S, Grotendorst G R, Daniels J T. Involvement of CTGF in TGF-beta1-stimulation of myofibroblast differentiation and collagen matrix contraction in the presence of mechanical stress. *Invest Ophthalmol Vis Sci* 2004; 45(4):1109-16.

Ghahary A, Shen Y J, Scott P G, Gong Y, Tredget E E. Enhanced expression of mRNA for transforming growth factor-beta, type I and type III procollagen in human postburn hypertrophic scar tissues. *J Lab Clin Med* 1993; 122 (4):465-73.

Grotendorst G R, Rahmanie H, Duncan M R. Combinatorial signaling pathways determine fibroblast proliferation and myofibroblast differentiation. *Faseb J* 2004; 18(3):469-79.

Grotendorst G R. Connective tissue growth factor: a mediator of TGF-beta action on fibroblasts. *Cytokine Growth Factor Rev* 1997; 8(3):171-9.

Harrop A R, Ghahary A, Scott P G, Forsyth N, Uji-Friedland A, Tredget E E. Regulation of collagen synthesis and mRNA expression in normal and hypertrophic scar fibroblasts in vitro by interferon-gamma. *J Surg Res* 1995; 58(5):471-7.

Hinz B, Mastrangelo D, Iselin C E, Chaponnier C, Gabbiani G. Mechanical tension controls granulation tissue contractile activity and myofibroblast differentiation. *The American journal of pathology* 2001; 159(3):1009-20.

Igarashi A, Nashiro K, Kikuchi K, Sato S, Ihn H, Fujimoto M, et al. Connective tissue growth factor gene expression in tissue sections from localized scleroderma, keloid, and other fibrotic skin disorders. *The Journal of investigative dermatology* 1996; 106(4):729-33.

Igarashi A, Okochi H, Bradham D M, Grotendorst G R. Regulation of connective tissue growth factor gene expression in human skin fibroblasts and during wound repair. *Mol Biol Cell* 1993; 4(6):637-45.

Ivkovic S, Yoon B S, Popoff S N, Safadi F F, Libuda D E, Stephenson R C, et al. Connective tissue growth factor coordinates chondrogenesis and angiogenesis during skeletal development. *Development* (Cambridge, England) 2003; 130(12):2779-91.

Kessler D, Dethlefsen S, Haase I, Plomann M, Hirche F, Krieg T, et al. Fibroblasts in mechanically stressed collagen lattices assume a "synthetic" phenotype. *J Biol Chem* 2001; 276(39):36575-85.

Kryger Z B, Sisco M, Roy N K, Lu L, Rosenberg D, Mustoe T A. Temporal expression of the transfo ming growth factor-Beta pathway in the rabbit ear model of wound healing and scarring. *J Am Coll Surg* 2007; 205(1):78-88.

Leask A, and Abraham D J. TGF-beta signaling and the fibrotic response. *Faseb J* 2004; 18(7):816-27.

Li G, Xie Q, Shi Y, Li D, Zhang M, Jiang S, et al. Inhibition of connective tissue growth factor by siRNA prevents liver fibrosis in rats. *The journal of gene medicine* 2006; 8(7): 889-900.

Lin C G, Chen C C, Leu S J, Grzeszkiewicz T M, Lau L F. Integrin-dependent functions of the angiogenic inducer NOV (CCN3): implication in wound healing. *J Biol Chem* 2005; 280(9):8229-37.

Lu L, Saulis A S, Liu W R, Roy N K, Chao J D, Ledbetter S, et al. The temporal effects of anti-TGF-beta1, 2, and 3 monoclonal antibody on wound healing and hypertrophic scar formation. *J Am Coll Surg* 2005; 201(3):391-7.

Marcus J R, Tyrone J W, Bonomo S, Xia Y, Mustoe T A. Cellular mechanisms for diminished scarring with aging. *Plast Reconstr Surg* 2000; 105(5):1591-9.

McKay R A, Miraglia L J, Cummins L L, Owens S R, Sasmor H, Dean N M. Characterization of a potent and specific class of antisense oligonucleotide inhibitor of human protein kinase C-alpha expression. *J Biol Chem* 1999; 274(3): 1715-22.

Mori T, Kawara S, Shinozaki M, Hayashi N, Kakinuma T, Igarashi A, et al. Role and interaction of connective tissue growth factor with transforming growth factor-beta in persistent fibrosis: A mouse fibrosis model. *J Cell Physiol* 1999; 181(1):153-9.

Morris D E, Wu L, Zhao L L, Bolton L, Roth S I, Ladin D A, et al. Acute and chronic animal models for excessive dermal scarring: quantitative studies. *Plast Reconstr Surg* 1997; 100(3):674-81.

Mustoe T A, Pierce G F, Morishima C, Deuel T F. Growth factor-induced acceleration of tissue repair through direct and inductive activities in a rabbit dermal ulcer model. *J Clin Invest* 1991; 87(2):694-703.

Mustoe T A. Scars and keloids. *BMJ Clinical research* ed 2004; 328(7452):1329-30.

Reid R R, Mogford J E, Butt R, deGiorgio-Miller A, Mustoe T A. Inhibition of procollagen C-proteinase reduces scar hypertrophy in a rabbit model of cutaneous scarring. *Wound Repair Regen* 2006; 14(2):138-41.

Riser B L, Denichilo M, Cortes P, Baker C, Grondin J M, Yee J, et al. Regulation of connective tissue growth factor activity in cultured rat mesangial cells and its expression in experimental diabetic glomerulosclerosis. *J Am Soc Nephrol* 2000; 11(1):25-38.

Saulis A S, Mogford J H, Mustoe T A. Effect of Mederma on hypertrophic scarring in the rabbit ear model. *Plast Reconstr Surg* 2002; 110(1):177-83; discussion 84-6.

Schild C, Trueb B. Mechanical stress is required for high-level expression of connective tissue growth factor. *Exp Cell Res* 2002; 274(1):83-91.

Shah M, Foreman D M, Ferguson M W. Control of scarring in adult wounds by neutralising antibody to transforming growth factor beta. *Lancet* 1992; 339(8787):213-4.

Shah M, Foreman D M, Ferguson M W. Neutralisation of TGF-beta 1 and TGF-beta 2 or exogenous addition of TGF-beta 3 to cutaneous rat wounds reduces scarring. *Journal of cell science* 1995; 108 (Pt 3):985-1002.

Shah M, Foreman D M, Ferguson M W. Neutralising antibody to TGF-beta 1, 2 reduces cutaneous scarring in adult rodents. *J Cell Sci* 1994; 107 (Pt 5):1137-57.

Shi-wen X, Pennington D, Holmes A, Leask A, Bradham D, Beauchamp J R, et al. Autocrine overexpression of CTGF maintains fibrosis: RDA analysis of fibrosis genes in systemic sclerosis. *Exp Cell Res* 2000; 259(1):213-24.

Shull M M, Ormsby I, Kier A B, Pawlowski S, Diebold R J, Yin M, et al. Targeted disruption of the mouse transforming growth factor-beta 1 gene results in multifocal inflammatory disease. *Nature* 1992; 359(6397):693-9.

Sisco M, Kryger Z B, Jia S C, Schultz G S, Dean N M, Mustoe T A. Antisense oligonucleotides against transforming growth factor-beta delay wound healing in a rabbit ear model. *J Am Coll Surg* 2005; 201:S60.

Tomasek J J, Gabbiani G, Hinz B, Chaponnier C, Brown R A. Myofibroblasts and mechano-regulation of connective tissue remodelling. *Nat Rev Mol Cell Biol* 2002; 3(5):349-63.

Wang J F, Olson M E, Ma L, Brigstock D R, Hart D A. Connective tissue growth factor siRNA modulates mRNA levels for a subset of molecules in normal and TGF-beta 1-stimulated porcine skin fibroblasts. *Wound Repair Regen* 2004; 12(2):205-16.

Zhang H, Cook J, Nickel J, Yu R, Stecker K, Myers K, et al. Reduction of liver Fas expression by an antisense oligonucleotide protects mice from fulminant hepatitis. *Nat Biotechnol* 2000; 18(8):862-7. Reid R R, Mogford J E, Butt R, deGiorgio-Miller A, Mustoe T A. Inhibition of procollagen C-proteinase reduces scar hypertrophy in a rabbit model of cutaneous scarring. *Wound Repair Regen* 2006; 14(2):138-41.

What is claimed is:

1. A method for reducing hypertrophic scarring resulting from dermal wound healing in a subject in need thereof which comprises administering directly to the subject's wound an antisense compound which targets a nucleic acid encoding, and inhibits expression of, connective tissue growth factor (CTGF) in an amount effective to inhibit expression of CTGF and thereby reduce hypertrophic scarring, wherein the antisense compound comprises an antisense oligonucleotide comprising a nucleotide sequence selected from the group consisting of SEQ ID NO:1 and SEQ ID NO:2, wherein the antisense compound is to be administered intermittently with each subsequent administration being effected at least 4 days after the prior administration and wherein the antisense compound is administered in an amount effective to reduce scarring without having an adverse effect on wound healing.

2. A method for reducing hypertrophic scarring resulting from dermal wound healing in a subject in need thereof which comprises administering directly to the subject's wound an antisense compound which targets a nucleic acid encoding, and inhibits expression of, connective tissue growth factor (CTGF) in an amount effective to inhibit expression of CTGF and thereby reduce hypertrophic scarring, wherein the antisense compound comprises an antisense oligonucleotide comprising a nucleotide sequence selected from the group consisting of SEQ ID NO:1 and SEQ ID NO:2, wherein the antisense compound is to be administered in an amount effective to reduce scarring without having an adverse effect on wound healing.

3. The method of claim 2, wherein the antisense oligonucleotide is a modified antisense oligonucleotide comprising 20 to 30 linked nucleosides targeted to a nucleic acid encoding connective tissue growth factor, wherein the oligonucleotide specifically hybridizes with said nucleic acid and inhibits expression of connective tissue growth factor, wherein said oligonucleotide comprises at least one modification selected from the group consisting of a modified internucleoside linkage, a modified sugar, and a modified nucleobase.

4. The method of claim 3, wherein the antisense oligonucleotide comprises at least one modified internucleoside linkage.

5. The method of claim 4, wherein the modified internucleoside linkage is a phosphorothioate linkage.

6. The method of claim 3, wherein the antisense compound is administered commencing no sooner than 7 days after the subject is wounded.

7. The method of claim 6, wherein the antisense compound is administered commencing about 14 days after the subject is wounded and continuing thereafter during the period of wound healing and scarring.

8. The method of claim 3, wherein the antisense compound is administered commencing immediately before or after the subject is wounded.

9. The method of claim 3, wherein the antisense oligonucleotide comprises at least one modified nucleobase.

10. The method of claim 9, wherein the modified nucleobase is a 5-methylcytosine.

11. The method of claim 2, wherein the antisense oligonucleotide comprises at least one modified sugar.

12. The method of claim 11, wherein the modified sugar is a 2'-0-methoxyethyl sugar.

13. The method of claim 2, further comprising administering to the subject a second antisense oligonucleotide which targets a nucleic acid encoding, and inhibits expression of, connective tissue growth factor.

14. The method of claim 2, wherein the amount of antisense compound administered is between 100 µg/cm and 10 mg/cm of the wound.

15. The method of claim 14, wherein the amount of antisense compound administered is above 300 µg/cm.

16. The method of claim 2, further comprising administering to the subject an antisense oligonucleotide which targets a nucleic acid encoding, and inhibits expression of, transforming growth factor β1 (TGF-β1) in an amount effective to inhibit expression of TGF-β1, wherein the antisense oligonucleotide to TGF-β1 comprises a nucleotide sequence of SEQ ID NO:3.

* * * * *